US 11,219,560 B2

(12) United States Patent
Villarreal

(10) Patent No.: US 11,219,560 B2
(45) Date of Patent: Jan. 11, 2022

(54) MALE INCONTINENCE PAD

(71) Applicant: Vivian Louise Villarreal, Edinburg, TX (US)

(72) Inventor: Vivian Louise Villarreal, Edinburg, TX (US)

(*) Notice: Subject to any disclaimer, the term of this patent is extended or adjusted under 35 U.S.C. 154(b) by 180 days.

(21) Appl. No.: 16/521,831

(22) Filed: Jul. 25, 2019

(65) Prior Publication Data

US 2021/0154055 A1 May 27, 2021

Related U.S. Application Data

(63) Continuation-in-part of application No. 15/165,774, filed on May 26, 2016, now Pat. No. 10,406,039.

(60) Provisional application No. 62/166,486, filed on May 26, 2015.

(51) Int. Cl.
*A61F 13/471* (2006.01)
*A61F 5/453* (2006.01)
*A61F 5/44* (2006.01)
*A61F 13/56* (2006.01)

(52) U.S. Cl.
CPC .......... *A61F 13/471* (2013.01); *A61F 5/4401* (2013.01); *A61F 5/453* (2013.01); *A61F 13/5611* (2013.01)

(58) Field of Classification Search
CPC .......... A61F 5/44; A61F 5/4401; A61F 5/451; A61F 5/453; A61F 2005/4402; A61F 13/471; A61F 13/4915; A61F 13/51113; A61F 2013/51117
See application file for complete search history.

(56) References Cited

U.S. PATENT DOCUMENTS

| | | | |
|---|---|---|---|
| 4,886,509 A | 12/1989 | Mattsson | |
| 6,105,174 A | 8/2000 | Nygren | |
| 6,129,719 A | 10/2000 | Nozaki et al. | |
| 6,197,011 B1* | 3/2001 | Freitas | A61F 13/471 |
| | | | 604/385.03 |
| 6,209,142 B1* | 4/2001 | Mattsson | A61F 5/453 |
| | | | 2/400 |
| 6,336,919 B1 | 1/2002 | Davis | |
| 6,530,909 B1 | 3/2003 | Nozaki | |
| 6,569,135 B1 | 5/2003 | Mula | |
| 6,817,992 B1* | 11/2004 | Sassak | A61F 5/453 |
| | | | 604/349 |
| 6,910,137 B2 | 6/2005 | Liebenow et al. | |

(Continued)

FOREIGN PATENT DOCUMENTS

JP 2008-23247 2/2008
WO WO 99/33422 7/1999

OTHER PUBLICATIONS

International Search Report for corresponding PCT application: PCT/US20/42979.

(Continued)

*Primary Examiner* — Catharine L Anderson
(74) *Attorney, Agent, or Firm* — Mark F. Smith; Smith Brandenburg Ltd.

(57) ABSTRACT

Male incontinence pad having an outer absorbent pad, an inner lining and an inner adsorbent pad, each having an aperture that together form a channel for receiving a male member. The male incontinence pad is folded around the male member to form a pocket that in use operates to absorb any discharge from the male member.

18 Claims, 19 Drawing Sheets

(56) References Cited

U.S. PATENT DOCUMENTS

| | | |
|---|---|---|
| 8,702,667 B1 | 4/2014 | Johnson |
| 2011/0015604 A1 | 1/2011 | Back |
| 2012/0308787 A1 | 12/2012 | Kozee et al. |
| 2016/0008188 A1 | 1/2016 | Lumaque-Steeman |
| 2016/0346137 A1 | 12/2016 | Villrreal |
| 2017/0165100 A1 | 6/2017 | Jackson |
| 2017/0202714 A1* | 7/2017 | Hurwitz ................ A61F 13/475 |

OTHER PUBLICATIONS

International Search Report, dated Sep. 2, 2016, PCT Patent Application No. PCT/US16/34375, Int. Filing Date: May 26, 2016.

Written Opinion of Int. Search Authority, dated Sep. 2, 2016, PCT Patent Application No. PVT?US16/34375, Int. Filing Date: May 26, 2016.

Office Action for U.S. Patent No. U.S. Appl. No. 15/165,774, dated May 26, 2016.

* cited by examiner

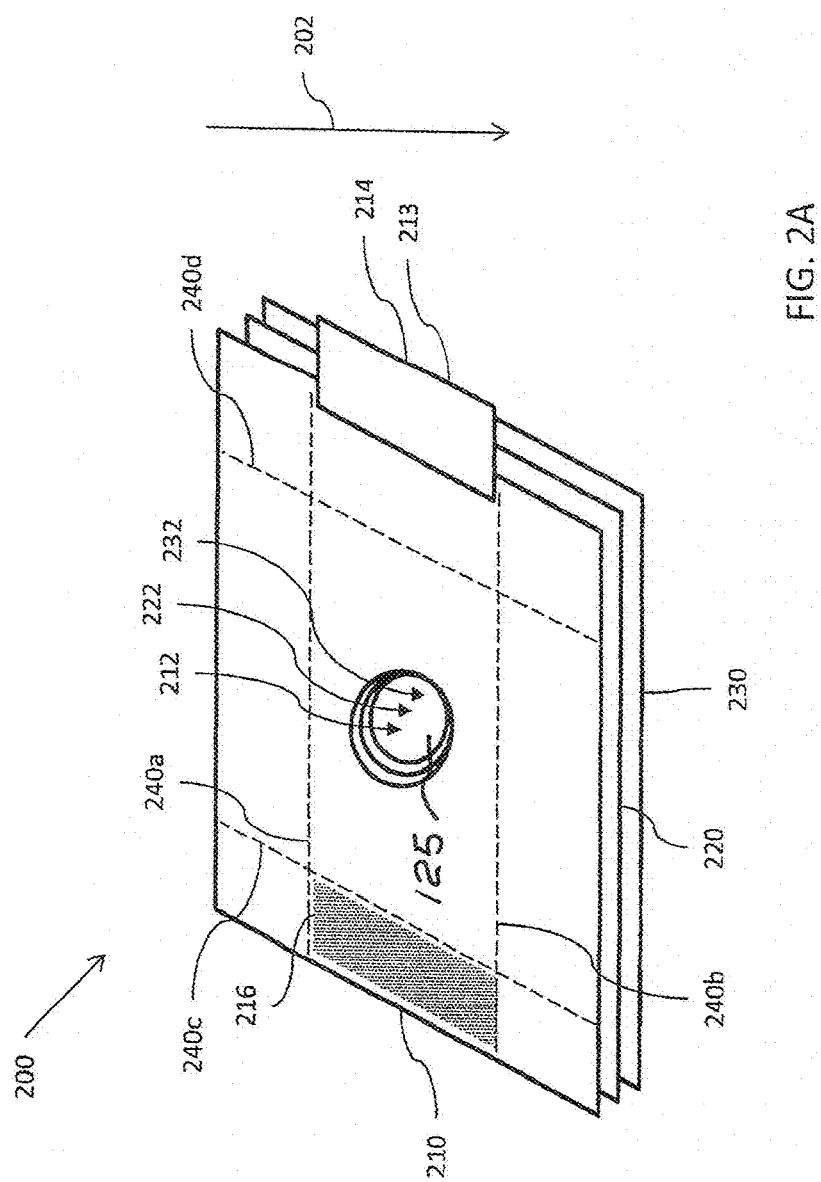

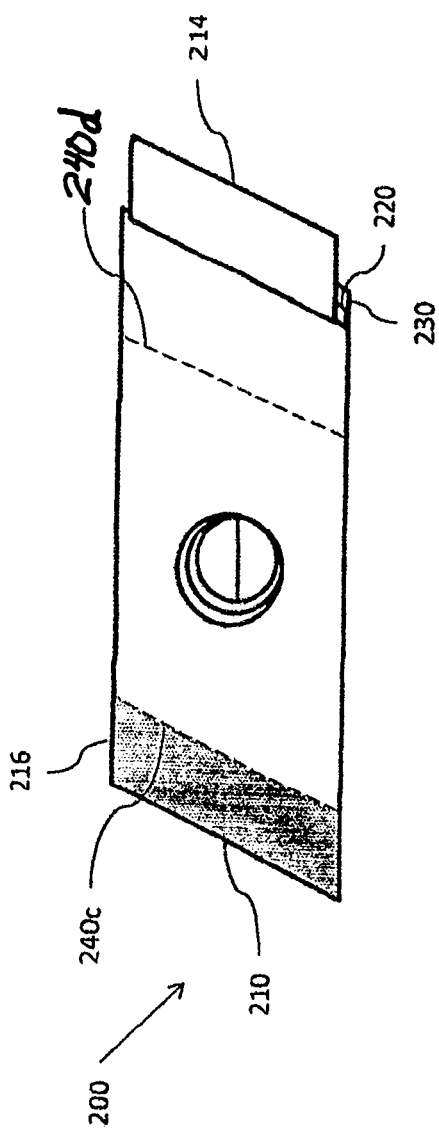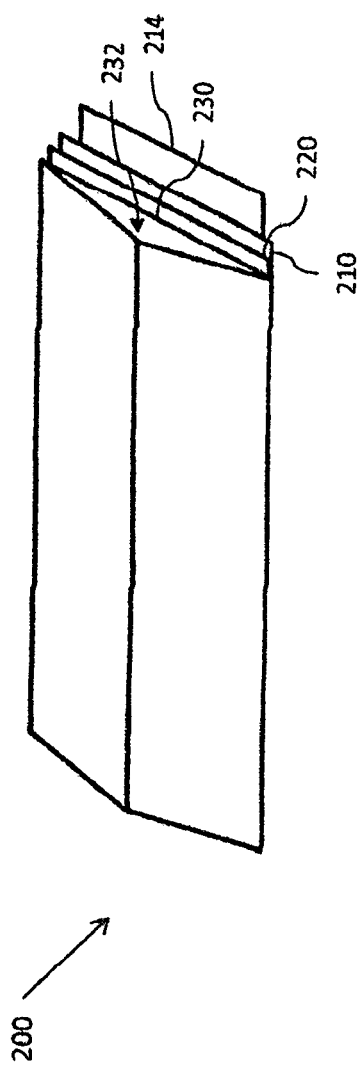
FIG. 2C
FIG. 2C'

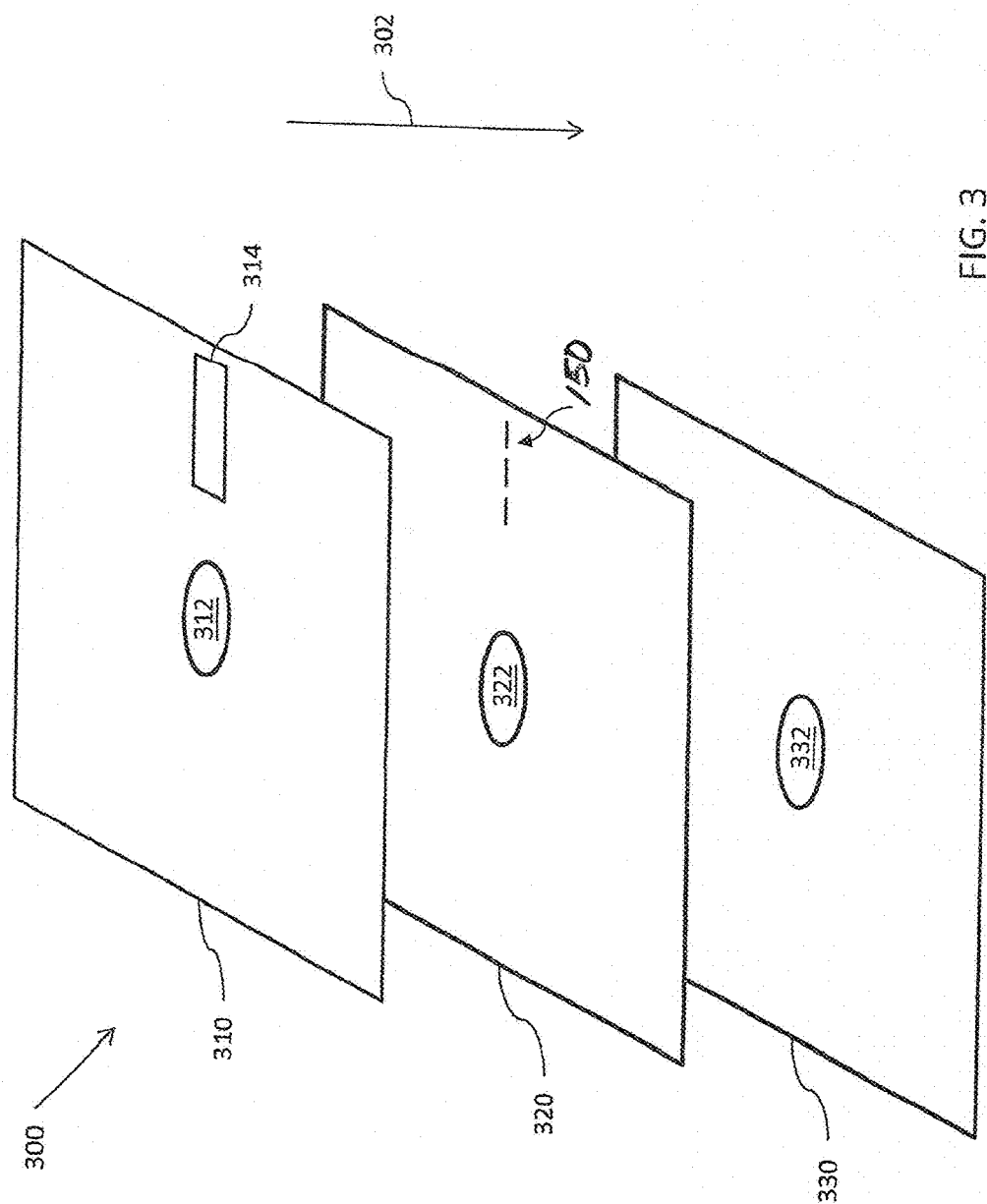

614

616

MALE INCONTINENCE PAD

RELATED APPLICATIONS

This application is a Continuation-In-Part of U.S. patent application Ser. No. 15/165,774, filed May 26, 2016 which claims priority to and the benefit of U.S. Patent Application No. 62/166,486, filed May 26, 2015. The prior applications are herein incorporated by reference in their entirety.

BACKGROUND OF THE INVENTION

Adult humans can become paralyzed due to a variety of reasons (e.g., falls, car accidents, gunshots, etc.). For example, there are between 250,000 and 350,000 people living in the United States with spinal cord injuries, and there are approximately 12,000 new cases each year. Improved emergency care for people with spinal cord injuries and aggressive treatment and rehabilitation can minimize damage to the nervous system and even restore some function to the patient.

Spinal cord injury primarily affects young adults. The average age of injury is 41 years old, and over 80% of spinal cord injuries occur among males.

For people dealing with paralysis in the lower part of their body, managing the discharge of bodily waste is typically a constant issue. Often, such people wear adult-sized incontinence briefs, which can be changed when they are soiled.

SUMMARY OF THE INVENTION

Male incontinence pads may be formed and used by a variety of techniques. In particular implementations, a male incontinence pad may include a first absorbent pad, a second absorbent pad, and a water impermeable lining. The water impermeable lining may be between the pads, and the first absorbent pad, the second absorbent pad, and the lining may each include an aperture that are aligned to allow a male member to be placed therethrough. The second absorbent pad may be adapted to be folded to form a pocket for the male member.

A preferred embodiment of the invention is a male incontinence pad for use by a male wearer, the male incontinence pad comprises an inner absorbent pad; an outer absorbent pad; wherein the outer absorbent pad and the inner absorbent pad are attached together having an open end forming an inner pocket and an outwardly extending flap; wherein the inner absorbent pad and the outer absorbent pad having apertures that form a channel that extends into the inner pocket; wherein when a male member is inserted through the channel the male member extends into the inner pocket; and wherein when the male member extends into the inner pocket, the outwardly extending flap operates to fold over the male member.

In a preferred embodiment of the invention the inner absorbent pad and the outer absorbent pad operate to fold around the male member and includes a fastening system for maintaining the inner absorbent pad and the outer absorbent pad in position folded around the male member.

In a preferred embodiment of the invention the inner absorbent pad includes a liquid permeable layer and a wicking layer and a SP core layer.

In a preferred embodiment of the invention the outer absorbent pad includes an outer attachment layer attached to a liquid impermeable layer and wherein the liquid impermeable layer is attached to a SAP core layer.

One or more male incontinence pads may have one or more features. For example, a pad may be able to substantially (or maybe even completely) absorb discharge from a wearer. Thus, when it is time to tend to the wearer, the task is much easier, as the pad may be removed simply and only minimal cleanup around the male member may be required. Moreover, a new pad may be readily fitted. When a wearer only uses a full-size incontinence brief, the entire brief must be changed, which requires a substantial amount of physical effort. Moreover, for individuals that require regular hydration (e.g., through a IV), this may mean that they need to be tended to every few hours. Having to change a full-size brief every few hours is a very labor-intensive task. Additionally, the pad may prevent bed sores in the groin area due to the fact that the patient would not have to lie wet with urine for long periods of time in the region surrounding the entire groin area. This is especially true if the pad is being changed frequently, as it should be, which may be more likely since the changing process is greatly simplified. Moreover, the pad may cost quite a bit less than a typical incontinence brief, which may save the caregiver money.

In preferred embodiments of the invention, the incontinence pad includes an elastic component positioned around the periphery of the channel formed from apertures in the outer pad, lining and inner pad for receiving a male member and operates to expand or contract to maintain contact of the pad around the male member.

In preferred embodiments of the invention the outer pad includes a skin care agent that operates to suppress the occurrence of rash and inflammation and if rash or inflammation occurs, suppresses the progress of the rash or inflammation or relaxes the rash or inflammation.

In preferred embodiments of the invention the skin care agent includes copper or a copper alloy that operates to reduce the growth of bacteria.

In preferred embodiments of the invention the skin care agent is in the form of copper or copper alloy threads or fibers.

In preferred embodiments of the invention the skin care agent is in the form of coper or copper alloy powder.

A variety of other features will be apparent to one of skill in the art from the following description, the figures, and the claims.

BRIEF DESCRIPTION OF THE DRAWINGS

FIG. 2A is a line drawing illustrating a second example male incontinence pad at one strep of operation.

FIG. 2C is a line drawing illustrating the second example male incontinence pad at an additional step of operation.

FIG. 2C' is a line drawing illustrating the reverse side of the pad in FIG. 2C.

FIG. 3 is a line drawing illustrating an exploded view of a third example male incontinence pad.

DESCRIPTION OF THE INVENTION

Figure 1A:
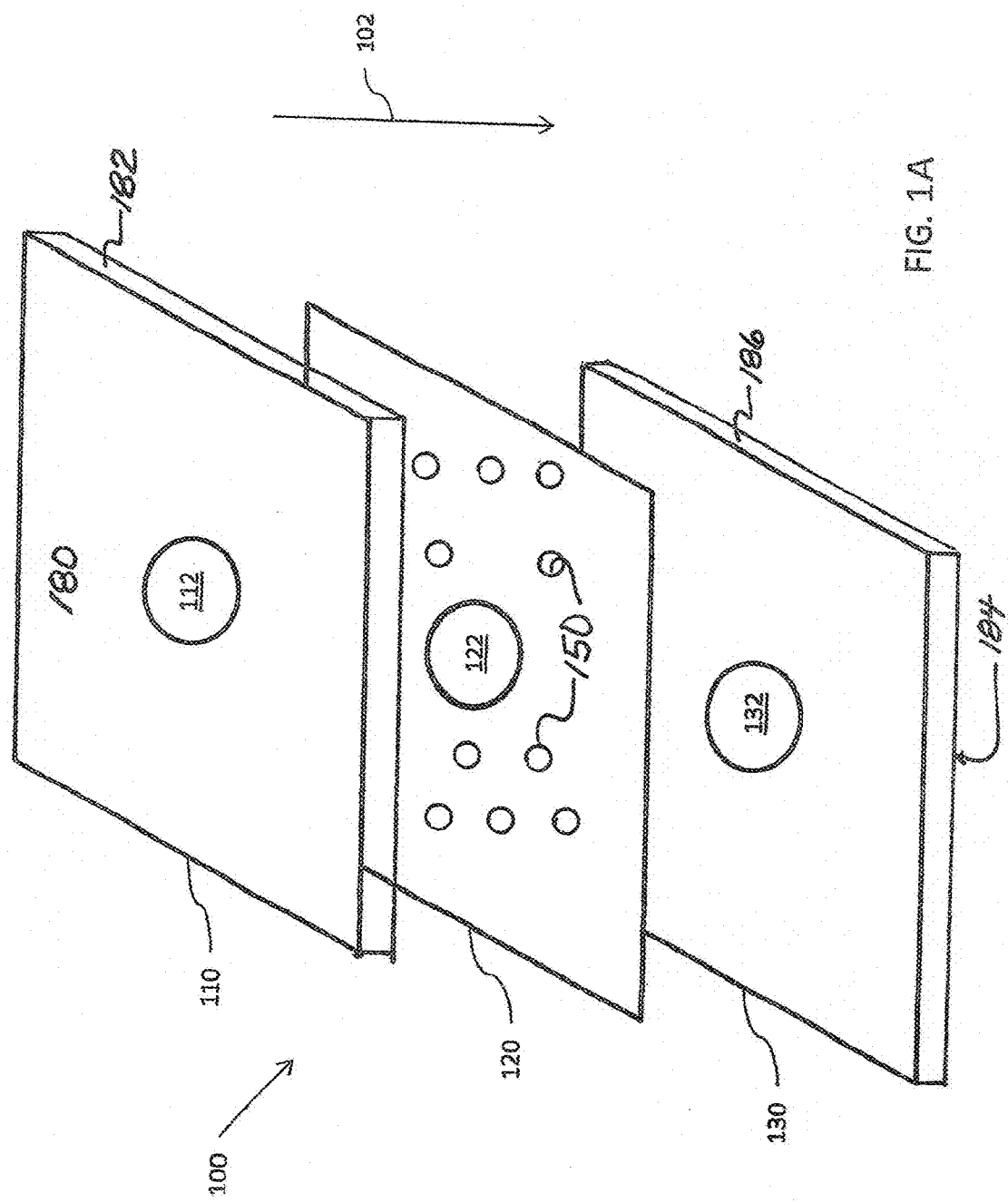
FIG. 1A is a line drawing illustrating an exploded view of an example male incontinence pad.
Figure 1B:
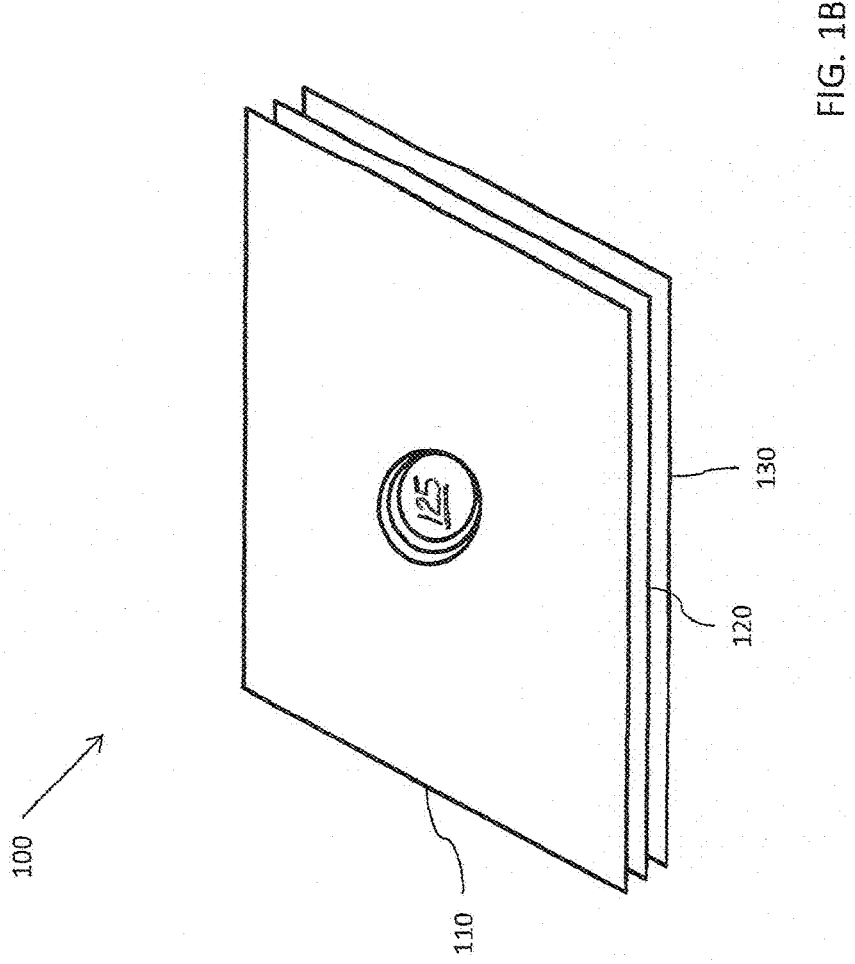
FIG. 1B is a line drawing illustrating a partially assembled view of the example male incontinence pad.
Figure 2B:
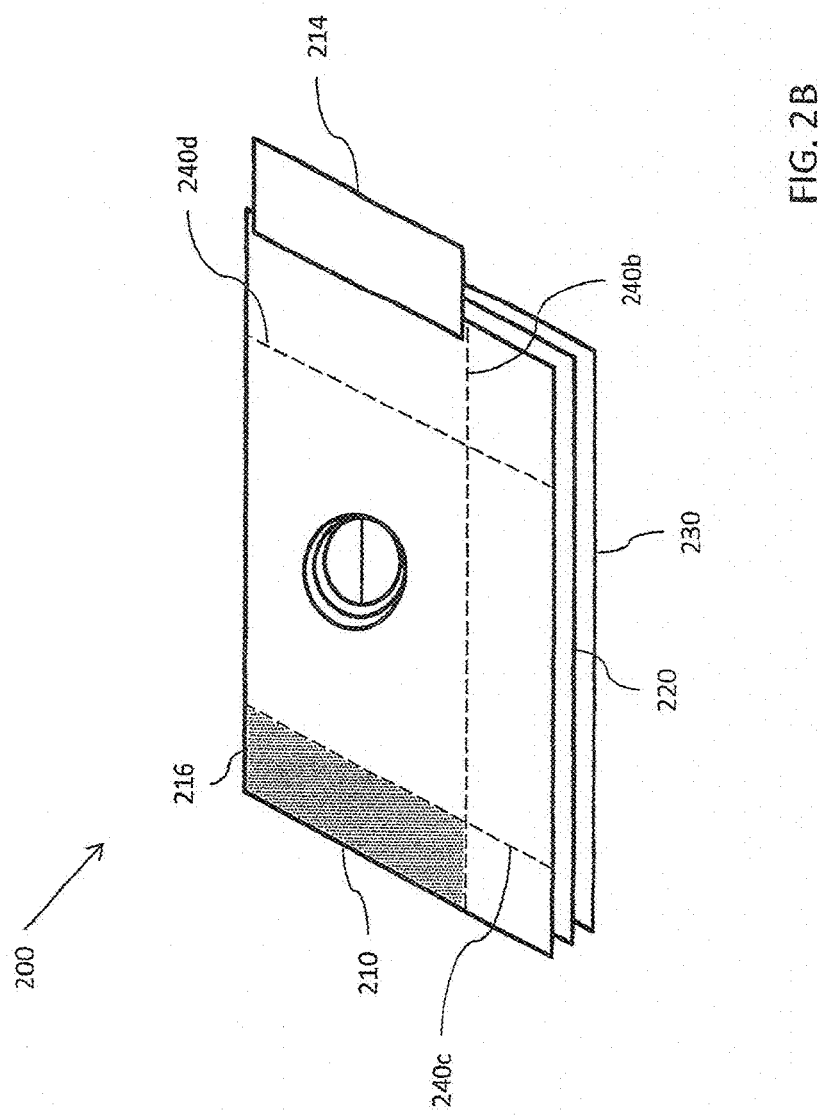
FIG. 2B is a line drawing illustrating the second example male incontinence pad at another step of operation.
Figure 2D:
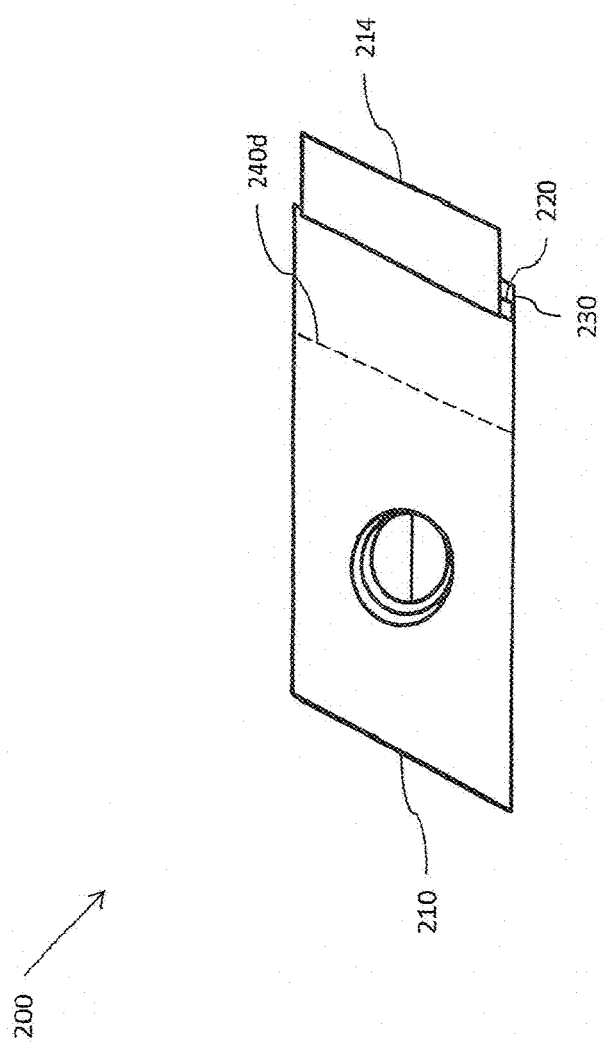
FIG. 2D is a line drawing illustrating the second example male incontinence pad at a further step of operation.
Figure 2E:
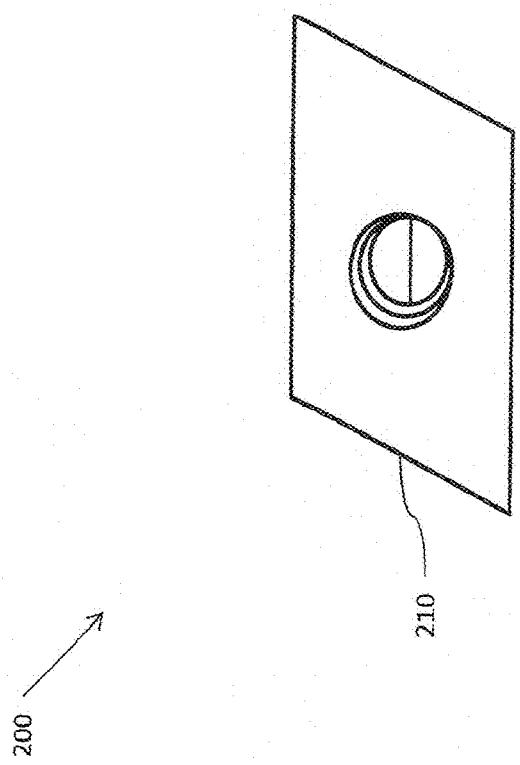
FIG. 2E is a line drawing illustrating the second example male incontinence pad at yet another step of operation.

FIGS. 1A-1B illustrate an example male incontinence pad 100. Among other things, pad 100 includes an outer absorbent pad 110, an inner lining 120, and an inner absorbent pad 130.

As illustrated, male incontinence pad 100 is generally square. Pad 100 could have a variety of sizes (8"×8", 12"×12", 16×16", etc.). Pad 100 could also have other shapes (e.g., rectangular, oval, round, etc.) in other implementations.

Outer absorbent pad 110, inner lining 120, and inner absorbent pad 130 include apertures 112, 122, and 132, respectively, through which a male member may be inserted (extending from the outer surface of outer absorbent pad 110 to the other side of inner absorbent pad 130). As illustrated, apertures 112,122,132 are circular areas where material has been removed. Apertures 112,122,132 may typically between about 1-2" in length. In other implementations, apertures 112,122,132 may have other shapes (e.g., oval, rectangular, square, triangular, etc.). In certain implementations, apertures 112,122, and 132 may be slits in the respective materials (e.g., cuts).

Outer absorbent pad 110 may be made of any appropriate absorbent material. In certain implementations, outer absorbent pad 110 may have components similar to those of the inner layers of diapers or feminine napkins.

In particular implementations, outer absorbent pad 110 can be composed of an outer liquid permeable layer 180 and an inner absorbent layer 182. In certain implementations, the inner absorbent layer may be able to absorb about 200 times its own weight.

The inner absorbent layer 182 of the outer absorbent pad 110 can, for example, be made of cotton fibers or synthetic polymers. The inner absorbent layer can for, instance, be made of a hydrophilic polymer and a fibrous material such as wood pulp. The polymer can, for example, be made of fine particles of an acrylic acid derivative, such as sodium acrylate, potassium acrylate, or an alkyl acrylate. In certain implementations, the inner absorbent layer can be made of series 0570N700400 from Technical Absorbents Ltd. of North East Lincolnshire, York (UK). In another preferred embodiment the inner absorbent layer 182 can be formed from or include a super absorbent polymers or slush powders, hydrogels, or other super-absorbent material(s) (collectively referred to as SAP material) enclosed within the fibrous material or can be formed from a SAP material that operates to absorb and retain liquid discharge.

The outer liquid permeable layer can, for example, be made of a nonwoven fabric. Such nonwoven fabrics are typically made from plastic resins, such as nylon, polyester, polyethylene, or polypropylene, and are assembled by mechanically, chemically, or thermally interlocking the plastic fibers. Preferably, the methods of assembling nonwovens include wet laid process or a dry laid process, such as the "meltblown" method. In this method, the plastic resin is melted and extruded, or forced, through tiny holes by air pressure. As the air-blown stream of fibers cools, the fibers condense onto a layer. Heated rollers are then used to flatten the fibers and bond them together. In certain implementations, the outer liquid permeable layer can be made of polypropylene.

Inner lining 120 is preferably impermeable to liquid. Inner lining 120 can, for example, be made of a nonwoven fabric, such as plastic resins made from nylon, polyester, polyethylene, or polypropylene. In certain implementations.

Inner absorbent pad 130 can be made of any appropriate absorbent material. In certain implementations, inner absorbent pad 130 may have components similar to those of the inner layers of diapers or feminine napkins.

In particular implementations, inner absorbent pad 130 is composed of an outer permeable layer 184 and an inner absorbent layer 186. The inner absorbent layer 186 of inner absorbent pad 130 can be thinner than the absorbent layer 182 of outer absorbent pad 110.

The inner absorbent layer 186 of the inner absorbent pad 130 can, for example, be made of cotton fibers or synthetic polymers. The inner absorbent layer 186 can for, instance, be made of a hydrophilic polymer and a fibrous material such as wood pulp. The polymer can, for example, be made of fine particles of an acrylic acid derivative, such as sodium acrylate, potassium acrylate, or an alkyl acrylate. In certain implementations, the inner absorbent layer 186 may be made of series 0150N704300 from Technical Absorbents Ltd. In another preferred embodiment the inner absorbent layer 186 can be formed from or include a super absorbent polymers or slush powders, hydrogels, or other super-absorbent material(s) (collectively referred to as SAP material) enclosed within the fibrous material or can be formed from a SAP material that operates to absorb and retain liquid discharge. The outer liquid permeable layer 184 can be made of a nonwoven fabric.

Outer absorbent pad 110, inner lining 120, and inner absorbent pad 130 may be joined together by gluing, heating, or ultrasonic welding (e.g., along their periphery). In certain implementations, the periphery of the apertures 112, 122, 132 may also be joined so that the inner layers are sealed from the aperture.

In operation, the outer layer of outer absorbent pad 110 is positioned towards the wearer and moved to the groin area. The male member (i.e., penis) then is inserted through aperture 112, aperture 122, and aperture 132 which together form channel 125 (in the direction of arrow 102), and the pad is folded around the male member to make a pocket, primarily composed of inner absorbent pad 130.

For example, male incontinence pad 100 may folded on one side towards the distal end of the male member and then the opposite side towards the distal end of the male member. This causes inner absorbent pad 130 to form a pocket (e.g., partial for full) for the distal end of the male member. The edges of the folded portions of male incontinence pad 100 can be in proximity to each other or overlap each other. The incontinence pad 100 can then be folded along another side towards the distal end of the male member and then the opposite side towards the distal end of the male member, which will complete or reinforce the pocket for the male member. Portions of the pad from the third fold and from the fourth fold can be in proximity to each other or overlap each other. If desired, an incontinence brief can then be placed over the pad, which may better maintain the shape and/or position of the incontinence pad 100.

In particular implementations, outer absorbent pad 110 may include a fastening system, such as more fully described hereafter. The fastening system can, for example, include a first attachment zone and a second attachment zone. The attachment zones can, for instance, be parts of a hook-and-loop fastening system. In particular implementations, the attachment zones may be composed of a number of individual sections. In other implementations, the fastening system can include pins, snaps, and/or buttons.

During operation, the distal end of the male member should remain in the pocket formed by inner absorbent pad 130. Thus, if there is any discharge, the inner absorbent pad 130 operates to absorb this. Moreover, inner lining 120 operates to prevent or reduce the likelihood the discharge from reaching the wearer. If, however, the male member should come out from the pocket (e.g., due to movement or shrinkage), outer absorbent pad 110 operates to assist in absorbing any discharge. The absorbancy will typically not be as good as if the male member remained in the pocket, but the pad will operate to absorb all or a substantial portion of the discharge. In particular implementations, the outer absorbent pad 110 and inner absorbent pad 130 can absorb about 1.5 liters in combination.

Male incontinence pad 100 has a variety of features. For example, the pad operates to absorb or substantially absorb discharge from the wearer. Thus, when it is time to tend to the wearer, the task is much easier, as the pad may be removed simply and only minimal cleanup around the male member is required. Moreover, a new pad can be readily fitted. In contrast, when a wearer only uses a full-size incontinence brief, the entire brief must be changed, which requires a substantial amount of physical effort. Moreover, for individuals that require regular hydration (e.g., through an IV), this may mean that they need to be tended to every few hours. Having to change a full-size brief every few hours is a very labor-intensive task. The male incontinence pad of the subject invention operates to prevent or reduce bed sores in the groin area due to the fact that the pad can be easily changes thereby reducing the likelihood that the patient will have to lie wet with urine for long periods of time in the region surrounding the entire groin area. This is especially true if the pad is being changed frequently, as it should be, which will be more likely since the changing process is greatly simplified. Moreover, the pad may cost quite a bit less than a typical incontinence brief, which may save the caregiver money. Another benefit of the subject invention is that wearers would not have to rely as much on catheters, which can cause quite a bit of pain and discomfort and can lead to urinary tract infections.

Although FIGS. 1A-1B illustrate an example male incontinence pad, other embodiments of the male incontinence pad of the subject invention can have fewer, additional, or a different arrangement of components. For example, outer absorbent pad 110 can include a fastening system (e.g., one or more attachment zones), as more fully described herein. Moreover, an attachment zone can be placed on the inside of inner absorbent pad 130. Additionally, a different type of fastening system (e.g., pins) can be used. As another example, additional pads/layers can be used. In one example, inner absorbent pad 130 can have extra absorbency in the middle of the pad. Additionally, although four folds have been discussed for using the illustrated implementation, other modes of operation or implementations can allow for fewer or more folds.

In particular implementations, the inner liner 120 may have small openings (e.g., slits) 150 therein. These openings operate to allow liquid to flow from the inner absorbent pad 130 to the outer absorbent pad 110. By allowing liquid to flow from the inner absorbent pad 130 to the outer absorbent pad 110, the openings operate to assist in preventing leakage once the outer absorbent pad reaches its limit of absorption, by transferring the extra liquid into the inner absorbent pad. Additionally, the outer absorbent pad can include a wetness indicator 314, such as shown in FIG. 3, and the openings in the inner liner may allow the wetness indicator to function. Upon detecting wetness, the indicator operates to signal wetness, such as by a visual signal (e.g., color change). The wetness indicator can, for example, operate using a pH zone (e.g., litmus).

FIGS. 2A-E illustrate another example of the male incontinence pad 200 of the subject invention. Among other things, pad 200 includes an outer absorbent pad 210, an inner lining 220, and an inner absorbent pad 230. Male incontinence pad 200 may have features similar to those for male incontinence pad 100.

As illustrated, male incontinence pad 200 is generally square. Pad 200 can also have other shapes (e.g., rectangular, oval, round, etc.) in other implementations.

Outer absorbent pad 210, inner lining 220, and inner absorbent pad 230 include apertures 212, 222, and 232, respectively, that form a channel 125 through which a male member may be inserted (extending from the outer surface of outer absorbent pad 210 to the other side of inner absorbent pad 230). As illustrated, apertures 212, 222, 232 are circular areas where material has been removed. Apertures 212, 222, 232 may typically be between about 1-2" in length. In other implementations, apertures 212, 222, 232 may have other shapes (e.g., oval, rectangular, square, triangular, etc.). In certain implementations, apertures 212, 222, 232 may be slits in the respective materials (e.g., cuts).

Outer absorbent pad 210 can be made of any appropriate absorbent material. In certain implementations, outer absorbent pad 210 can have components similar to those of the inner layers of diapers or feminine napkins.

In particular implementations, outer absorbent pad 210 can be composed of an outer permeable layer 180 (such as shown in FIG. 1) and an inner absorbent layer 182 (such as shown in FIG. 1). The inner layer can, for example, be made of cotton fibers or synthetic polymers. The inner layer can for, instance, be made of a hydrophilic polymer and a fibrous material such as wood pulp. The polymer can, for example, be made of fine particles of an acrylic acid derivative, such as sodium acrylate, potassium acrylate, or an alkyl acrylate. In certain implementations, the inner layer can be made of series 0570N700400 from Technical Absorbents Ltd. In another preferred embodiment the inner absorbent layer 182 of the outer absorbent pad 210 can be formed from or include a super absorbent polymers or slush powders, hydrogels, or other super-absorbent material(s) (collectively referred to as SAP material) enclosed within the fibrous material or can be formed from a SAP material that operates to absorb and retain liquid discharge.

The outer permeable layer 180 can, for example, be made of a nonwoven fabric. Such nonwoven fabrics are made from plastic resins, such as nylon, polyester, polyethylene, or polypropylene, and are assembled by mechanically, chemically, or thermally interlocking the plastic fibers.

Inner lining 220 can be impermeable to liquid. Inner lining 220 can, for example, be made of a nonwoven fabric, such as plastic resins made from nylon, polyester, polyethylene, or polypropylene.

Inner absorbent pad 230 can be made of any appropriate absorbent material. In certain implementations, inner absorbent pad 230 can have components similar to those of the inner layers of diapers or feminine napkins.

In particular implementations, inner absorbent pad 230 can be composed of an outer permeable layer 184 and an inner absorbent layer 186 (such as shown in FIG. 1). The inner absorbent layer 186 can, for example, be made of cotton fibers or synthetic polymers. The inner layer can for, instance, be made of a hydrophilic polymer and a fibrous material such as wood pulp. The polymer can, for example, be made of fine particles of an acrylic acid derivative, such as sodium acrylate, potassium acrylate, or an alkyl acrylate. In certain implementations, the inner absorbent layer 186 can be made of series 0150N704300 from Technical Absorbents Ltd. In another preferred embodiment the inner absorbent layer can be formed from or include a super absorbent polymers or slush powders, hydrogels, or other super-absorbent material(s) (collectively referred to as SAP material) enclosed within the fibrous material or can be formed from a SAP material that operates to absorb and retain liquid discharge. The permeable layer 184 can be made of a nonwoven fabric.

Outer absorbent pad 210, inner lining 220, and inner absorbent pad 230 can be joined together by gluing, heating, or ultrasonic welding (e.g., along their periphery). In certain implementations, the periphery of the apertures 212, 222, 232 can be joined so that the inner layers are sealed from the aperture.

As illustrated, outer absorbent pad 210 also includes a fastening system 213, which includes an attachment zone 214 and an attachment zone 216. Attachment zone 214 can, for example, include one part of a hook-and-loop fastening system, and attachment zone 216 can include the other part. Although shown as being continuous, attachment zones 214, 216 can be composed of a number of individual sections.

In operation, the outer layer surface of outer absorbent pad 210 is positioned towards the wearer and moved to the groin area. The male member then is inserted through channel 125 formed by aperture 212, aperture 222, and aperture 232 (in the direction of arrow 202), and the male incontinence pad is folded along fold lines 240 around the male member to make a pocket 232.

Although fold lines are illustrated in FIGS. 2A-E, these may be for description only. That is, there may be no specifically prescribed lines along which to fold the male incontinence pad 200.

In the illustrated example, male incontinence pad 200 is folded on one side, along fold line 240a, and then the opposite side, along fold line 240b. This causes inner absorbent pad 230 to form a pocket (e.g., partial for full) for the distal end of the male member. The edges of the folded portions of the male incontinence pad 200 can be proximate each other or overlap each other. The male incontinence pad 200 is then folded along the side with attachment zone 216, along the fold line 240c, and then the side with attachment zone 214, along fold line 240d, which completes or reinforces the pocket 232 for the male member. Portions of the pad from the third fold and from the fourth fold can be proximate each other or overlap each other. Attachment zone 214 can then be coupled to attachment zone 216 so that the male incontinence pad maintains its folded shape. If desired, an incontinence brief can then be placed over the pad, which may better maintain the shape and/or position of make incontinence pad 200.

Although four folds are shown in the illustrated implementation, other modes of operation or implementations can allow for fewer of more folds.

During operation, the distal end of the male member should remain in the pocket formed by inner absorbent pad 230. Thus, if there is any discharge, inner absorbent pad 230 operates to absorb this. Moreover, inner lining 220 operates to prevent or reduce the likelihood of the discharge from reaching the wearer. If, however, the male member should come out from the pocket (e.g., due to movement or shrinkage), outer absorbent pad 210 operates to assist in absorbing any discharge. The absorbency will typically not be as be as good as if the male member remained in the pocket, but the pad will operate to absorb all or a substantial portion of the discharge.

Although FIGS. 2A-2E illustrate an example male incontinence pad, other suitable male incontinence pads can have fewer, additional, or a different arrangement of components. For example, outer absorbent pad 210 can include attachment zone 214 and/or attachment zone 216. An attachment zone can, for example, be placed on the inside of inner absorbent pad 230. Additionally, a different type of fastening system (e.g., pins) can be used. As another example, additional pads/layers can be used. In one example, inner absorbent pad 230 can have extra absorbency in the middle of the pad.

FIG. 3 illustrates an additional example male incontinence pad 300. Among other things, pad 300 includes an outer absorbent pad 310, an inner lining 320, and an inner absorbent pad 330.

As illustrated, male incontinence pad 300 is generally square. Pad 300 can also have other shapes (e.g., rectangular, oval, round, etc.) in other implementations.

Outer absorbent pad 310, inner lining 320, and inner absorbent pad 330 include apertures 312, 322, and 332, respectively, form a channel 125 through which a male member may be inserted (extending from the outer surface of outer absorbent pad 310 to the other side of inner absorbent pad 330). As illustrated, apertures 312, 322, 332 are oval areas where material has been removed. Apertures 312, 322, 332 typically will be between about 1-2" in length. In other implementations, apertures 312, 322, 332 may have other shapes (e.g., circular, rectangular, square, triangular, etc.). In certain implementations, apertures 312, 322, and 332 can be slits in the respective materials (e.g., cuts).

Outer absorbent pad 310 can be made of any appropriate absorbent material. In particular implementations, outer absorbent pad 310 can be composed of an outer permeable layer 180 and an inner absorbent layer 182 (such as shown in FIG. 1A).

Inner lining 320 may be impermeable to liquid. Inner lining 320 can, for example, be made of a nonwoven fabric, such as plastic resins made from nylon, polyester, polyethylene, or polypropylene.

Inner absorbent pad 330 can be made of any appropriate absorbent material. In particular implementations, inner absorbent pad 330 can be composed of an outer permeable layer 184 and an inner absorbent layer 186 (such as shown in FIG. 1A). The absorbent layer of inner absorbent pad 330 can be thinner than the absorbent layer of outer absorbent pad 310.

Outer absorbent pad 310, inner lining 320, and inner absorbent pad 330 can be joined together by gluing, heating, or ultrasonic welding (e.g., along their periphery). In certain implementations, the periphery of the apertures 312, 322, 332 can be joined so that the inner layers are sealed from the aperture.

As illustrated, inner lining 320 includes a number of openings 150 (e.g., slits) therein (as shown in FIGS. 1A and 3). If the openings are slits, they can, for example, be approximately 0.25"-1.25" long. In particular implementations, the slits may be approximately 0.75" long. Openings 150 operate to allow liquid flow from the inner absorbent pad 330 to the outer absorbent pad 310. By allowing liquid to flow from the outer absorbent pad 310 to the inner absorbent pad 330, the openings operate to assist in preventing leakage once the outer absorbent pad 330 reaches its limit of absorption, by conveying the extra liquid into the inner absorbent pad 310.

Outer absorbent pad 310 includes a wetness indicator 314. Wetness indicator 314 provides a signal, such as a visible indication (e.g., color change), when liquid is in outer absorbent pad 310, indicating that male incontinence pad 300 is wet or becoming full. The wetness indicator can, for example, use a pH technique (e.g., litmus) or any other appropriate technique.

In operation, the outer layer of outer absorbent pad 310 is positioned towards the wearer and moved to the groin area. The male member is then inserted through the channel 125 formed by aperture 312, aperture 322, and aperture 332 (in the direction of arrow 302), and the male incontinence pad is folded around the male member to make a pocket, primarily composed of inner absorbent pad 330.

For example, male incontinence pad 300 can be folded on one side that does have the wetness indicator 314 and then another side that does not have the wetness indicator. This causes inner absorbent pad 330 to form a pocket (e.g., partial for full) for the distal end of the male member. The edges of the folded portions of the male incontinence pad 300 can be in proximity to each other or overlap each other. The male incontinence pad 300 can then be folded along another side without the wetness indicator 314 and then along the side with the wetness indicator, resulting in the wetness indicator being visible when male incontinence pad 300 is on the wearer. Portions of the pad from the third fold and from the fourth fold can be in proximity to each other or overlap each other.

In particular implementations, two or more edges can be fastened to each other so that that the pad maintains its folded shape. For example, two edges can be pinned to each other or an attachment zone on one edge can be coupled to attachment zone on another edge (e.g., by hook and loop fasteners). If desired, an incontinence brief can then be placed over the pad, which may better maintain the shape and/or position of male incontinence pad 300.

During operation, the distal end of the male member should remain in the pocket formed by inner absorbent pad 330. Thus, if there is any discharge, inner absorbent pad 330 operates to absorb this. Moreover, inner lining 320 operates to prevent or reduce the likelihood of the discharge from reaching the wearer. If, however, the flow overwhelms the inner absorbent pad 330, the flow will leak into the outer absorbent pad 310 through openings 150. Thus, outer absorbent pad 310 provides backup fluid capture. Pads 310, 330 can absorb about 1.5 liters in combination. Additionally, once enough fluid enters outer absorbent pad 300, wetness indicator 314 will activate, informing the wearer or a caretaker that it is time to change the male incontinence pad 300.

Male incontinence pad 300 has a variety of features. For example, the pad can be able to completely or substantially absorb discharge from the wearer. Thus, when it is time to tend to the wearer, the task is much easier, as the pad can be removed simply and only minimal cleanup around the male member will be required. Moreover, a new pad can be readily fitted. In contrast, when a wearer only uses a full-size incontinence brief, the entire brief must be changed, which requires a substantial amount of physical effort. Moreover, for individuals that require regular hydration (e.g., through an IV), it may mean that they need to be tended to every few hours. Having to change a full-size brief every few hours is very labor-intensive task. The male incontinence pad of the subject invention operates to prevent or reduce bed sores in the groin area due to the fact that the pad is easy to replace and the patient will not have to lie wet with urine for long periods of time in the region surrounding the entire groin area. This is especially true if the pad is being change frequently, as it should be, which may be more likely since the changing process is greatly simplified. Moreover, the pad may cost quite a bit less than a typical incontinence brief, which may save the caregiver money. Another benefit of the male incontinence pad of the subject invention is that wearers will not have to rely as much on catheters, which can cause quite a bit of pain and discomfort and can lead to urinary tract infections.

Additionally, by allowing liquid to flow from the inner absorbent pad 330 to the outer absorbent pad 310, leakage can be prevented or minimized once the inner absorbent pad reaches its limit of absorption by absorbing the extra liquid in the outer absorbent pad. Furthermore, a wetness indication may be provided. These features can be used with other described incontinence pads.

Although FIG. 3, illustrates an example male incontinence pad of the subject invention, other exemplary male incontinence pads can have fewer, additional, or a different arrangement of components. For example, a pad can have multiple attachment zones. Additionally, additional layers can be used. In one example, inner absorbent pad 330 can have extra absorbency in the middle of the pad.

Figure 4A:
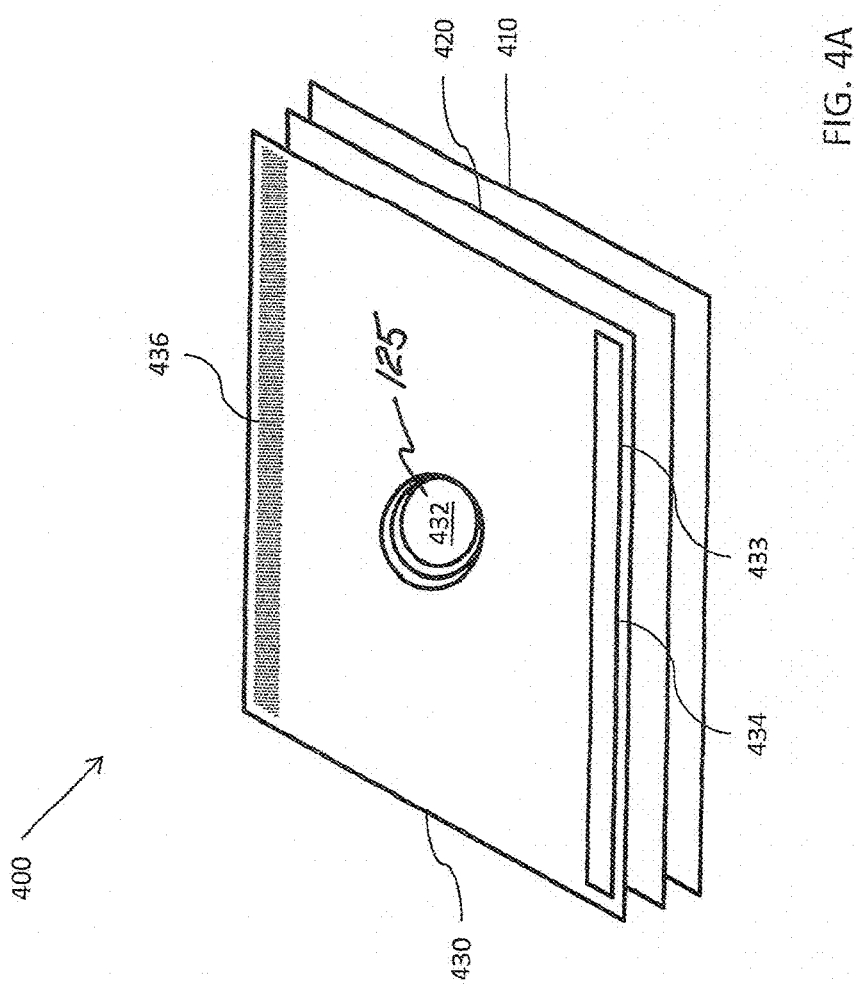
FIGS. 4A-4B are line drawings illustrating a fourth example male incontinence pad.
Figure 4B:
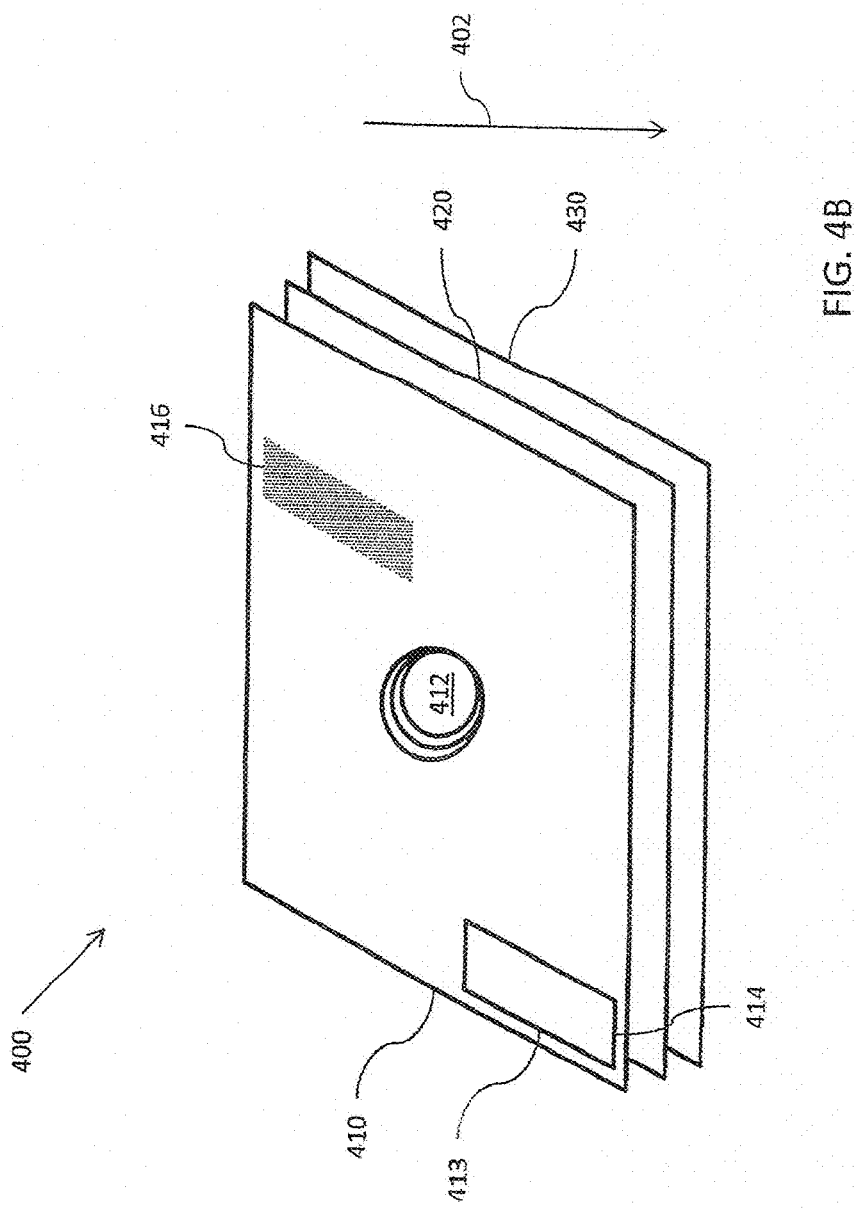

FIGS. 4A-4B illustrate another example male incontinence pad 400. Among other things, male incontinence pad 400 includes an outer absorbent pad 410, an inner lining 420, and an inner absorbent pad 430.

As illustrated, male incontinence pad 400 is generally square. Pad 400 can also have other shapes (e.g., rectangular, oval, round, etc.) in other implementations.

Outer absorbent pad 410, inner lining 420, and inner absorbent pad 430 include apertures 412, 422, and 432, respectively, that together form a channel 125 through which a male member may be inserted (extending from the outer surface of outer absorbent pad 410 to the other side of inner absorbent pad 430). As illustrated, apertures 412, 422, 432 are circular areas where material has been removed. Apertures 412, 422, 432 can typically be between about 1-2" in length. In other implementations, apertures 412, 422, 432 can have other shapes (e.g. oval, rectangular, square, triangular, etc.). In certain implementations, apertures 412, 422, and 432 may be slits (e.g., cuts) in the respective materials.

Outer absorbent pad 410 can be made of any appropriate absorbent material. In particular implementations, outer absorbent pad 410 can be composed of an outer permeable layer 180 and an inner absorbent layer 182 (such as shown in FIG. 1A). In certain implementations, the inner absorbent layer can absorb about 200 times its own weight.

Inner lining 420 can be impermeable to liquid. Inner lining 420 can, for example, be made of a nonwoven fabric, such as plastic resins made from nylon, polyester, polyethylene, or polypropylene.

Inner absorbent pad 430 can be made of any appropriate absorbent material. In particular implementations, inner absorbent pad 430 can be composed of an outer permeable layer and an inner absorbent layer. The absorbent layer of inner absorbent pad 430 can be thinner than the absorbent layer of outer absorbent pad 410.

Outer absorbent pad 410, inner lining 420, and inner absorbent pad 430 can be joined together by gluing, heating, or ultrasonic welding (e.g., along their periphery). In certain implementations, the periphery of the apertures 412, 422, 432 can be joined so that the inner layers are sealed from the aperture.

As illustrated, inner absorbent pad 430 includes a fastening system 433, which includes an attachment zone 434 and an attachment zone 436. Attachment zone 434 can, for example, include one part of a hook-and-loop fastener system, and attachment zone 436 can include the other part. In particular implementations, attachment zone 434 and attachment zone 436 can be composed of a number of individual sections.

Additionally, outer absorbent pad 410 includes a fastening system 413, which includes an attachment zone 414 and an attachment zone 416. Attachment zone 414 can, for example, include one part of a hook-and-loop fastener system, and attachment zone 416 can include the other part. In particular implementations, attachment zone 414 and attachments zone 416 can be composed of a number of individual sections.

In operation, the outer layer of outer absorbent pad 410 is positioned towards the wearer and moved to the groin area. The male member is then inserted through channel 125 formed by aperture 412, aperture 422, and aperture 432 (in the direction of arrow 402). Male incontinence pad 400 is then folded so that attachment zone 434 engages attachment zone 436, approximately folding pad 400 in half and establishing a partial pocket for the male member with inner absorbent pad 430. Then, the male incontinence pad 400 is folded into approximately thirds in the other direction, with the section containing attachment zone 416 being folded first so that attachment zone 414 may engage it. This completes the pocket around the male member.

During operation, the distal end of the male member should remain in the pocket formed by inner absorbent pad 430. Thus, if there is any discharge, inner absorbent pad 430 operates to absorb this. Moreover, inner lining 420 operates to prevent or reduce the likelihood of the discharge reaching the wearer. If, however, the male member should come out from the pocket (e.g., due to movement or shrinkage), outer absorbent pad 410 operates to assist in absorbing any discharge. The absorbency will typically not be as good as if the male member remained in the pocket, but the pad will operate to absorb all or a substantial portion of the discharge. In particular implementations, the two pads can absorb about 1.5 liters in combination.

Male incontinence pad 400 has a variety of features. For example, the pad can be able to substantially (or maybe even completely) absorb discharge from the wearer. Thus, when it is time to tend to the wearer, the task is much easier, as the pad can be removed simply and only minimal cleanup around the male member is required. Moreover, a new pad can be readily fitted. In contrast when a wearer only uses a full-size incontinence brief, the entire brief must be changed, which requires a substantial amount of physical effort. Moreover, for individuals that require regular hydration (e.g., through an IV), this may mean that they need to be tended to every few hours. Having to change a full-size brief every few hours may be a very labor-intensive task. The male incontinence pad of the subject invention operates to prevent or reduce the likelihood of bed sores in the groin area due to the fact that the pads are easily replaced and the patient will not have to lie wet with urine for long periods of time in the region surrounding the entire groin area. This is especially true if the pad is being changed frequently, as it should be, which is more likely since the changing process is greatly simplified. Moreover, the pad may cost quite a bit less than a typical incontinence brief, which may save the caregiver money. Another benefit is that wearers will not have to rely as much on catheters, which can cause quite a bit of pain and discomfort and can lead to urinary tract infections.

Although FIGS. 4A-4B illustrate an example incontinence pad, other exemplary male incontinence pads can have fewer, additional, or a different arrangement of components. For example, outer absorbent pad 410 can include attachment zone 414 and/or attachment zone 416. An attachment zone can, for example, be placed on the inside of inner absorbent pad 430. Additionally, a different type of fastener (e.g., pins) can be used. As another example, additional pads/layers can be used. In one example, inner absorbent pad 430 can have extra absorbency in the middle of the pad. Additionally, although four folds have been discussed for the illustrated implementation, other modes of operation or implementations can allow for fewer of more folds.

In particular implementations, the inner liner 420 can have small openings (e.g., slits) 150 therein, such as shown in FIGS. 1A and 3. These openings operate to allow liquid to flow from the inner absorbent pad 430 to the outer absorbent pad 410. By allowing liquid to flow from the inner absorbent pad 430 to the outer absorbent pad 410, the openings operate to assist in preventing leakage once the inner absorbent pad reaches its limit of absorption by leaking the extra liquid into the outer absorbent pad. Additionally, outer absorbent pad 410 can include a wetness indicator that activates in response to the liquid moving to the outer pad from the inner pad.

Figure 5:
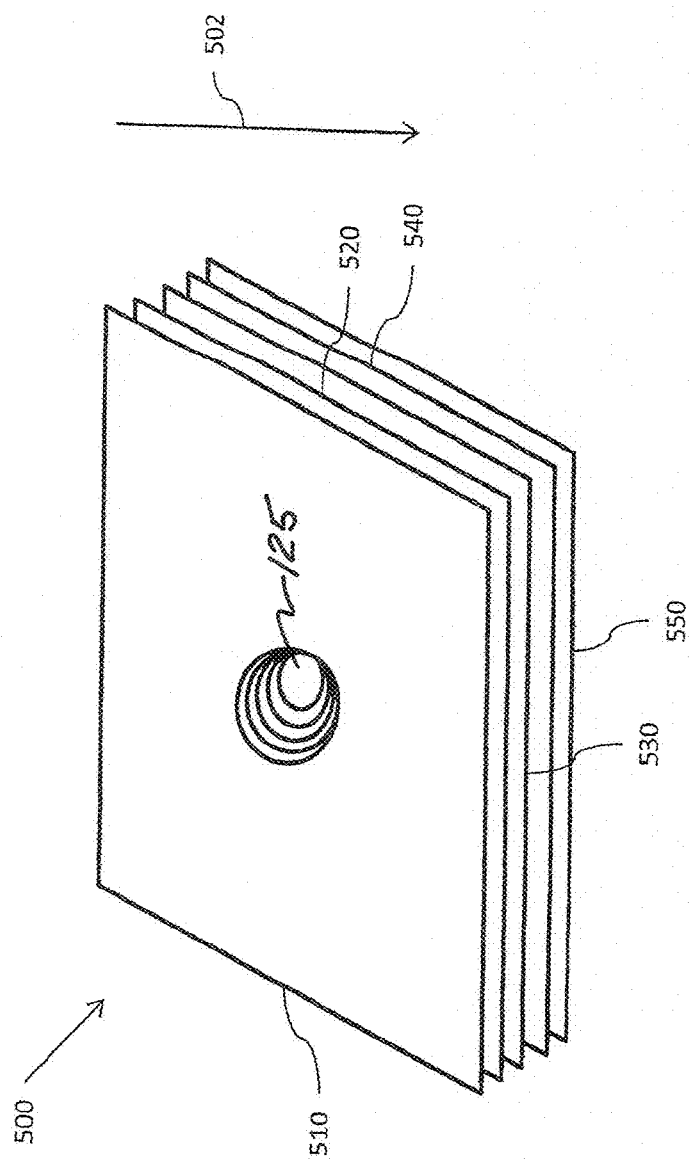
FIG. 5 is a line drawing illustrating a fifth example male incontinence pad.

FIG. 5 illustrates another example male incontinence pad 500 of the subject invention. Among other things, pad 500 includes an outer permeable layer 510, an inner absorbent layer 520, an inner lining 530, an inner absorbent layer 540, and an outer permeable layer 550.

As illustrated, pad 500 is generally square. Pad 500 can also have other shapes (e.g., rectangular, oval, round, etc.) in other implementations.

Outer permeable layer 510, inner absorbent layer 520, inner lining 530, inner absorbent layer 540, and outer permeable layer 550 include aligned apertures (not marked) that together form a channel 125 through which a male member may be inserted (extending from the outer surface of outer permeable layer 510 to the other side of outer permeable layer 550). As illustrated, the apertures form a circular channel. The channel is typically between about 1-2" in length. In other implementations, the channel can have another cross-sectional shape (e.g., oval, rectangular, square, triangular, etc.). In certain implementations, the apertures may be slits in the respective materials (e.g., cuts).

The outer permeable layer 510 and the inner absorbent layer 520 can form a pad. The pad can have components similar to those of the inner layers of diapers or feminine napkins.

The inner absorbent layer 520 can, for example, be made of cotton fibers or synthetic polymers. The inner absorbent layer can for, instance, be made of a hydrophilic polymer and a fibrous material such as wood pulp. The polymer can, for example, be made of fine particles of an acrylic acid derivative, such as sodium acrylate, potassium acrylate, or an alkyl acrylate. In certain implementations, the inner absorbent layer can be made of series 0570N700400 from Technical Absorbents Ltd. In another preferred embodiment the inner absorbent layer 520 can be formed from or include a super absorbent polymers or slush powders, hydrogels, or other super-absorbent material(s) (collectively referred to as SAP material) enclosed within the fibrous material or can be formed from a SAP material that operates to absorb and retain liquid discharge.

The outer permeable layer 510 can, for example, be made of a nonwoven fabric. In certain implementations, the permeable layer can be made of polypropylene.

Inner lining 530 can be impermeable to liquid. Inner lining 530 can, for example, also be made of a nonwoven fabric, such as plastic resins made from nylon, polyester, polyethylene, or polypropylene.

The outer permeable layer 550 and the inner absorbent layer 540 can form a pad. The pad can have components similar to those of the inner layers of diapers or feminine napkins.

The inner absorbent layer 540 can, for example, be made of cotton fibers or synthetic polymers. The inner layer can for, instance, be made of a hydrophilic polymer and a fibrous material such as wood pulp. The polymer can, for example, be made of fine particles of an acrylic acid derivative, such as sodium acrylate, potassium acrylate, or an alkyl acrylate. In certain implementations, the inner layer can be made of series 0150N704300 from Technical Absorbents Ltd. The inner absorbent layer 520 can be thinner than the outer absorbent layer 540. In another preferred embodiment the inner absorbent layer 540 can be formed from or include super absorbent polymers or slush powders, hydrogels, or other super-absorbent material(s) (collectively referred to as SAP material) enclosed within the fibrous material or can be formed from a SAP material that operates to absorb and retain liquid discharge. The outer permeable layer 550 layer can be made of a nonwoven fabric.

Outer permeable layer 510, inner absorbent layer 520, inner lining 530, inner absorbent layer 540, and outer permeable layer 550 can be joined together by gluing, heating, or ultrasonic welding (e.g., along their periphery). In certain implementations, the periphery of the apertures of the layers can also be joined so that the inner layers are sealed from the aperture.

In operation, outer permeable layer 510 is positioned towards the wearer and moved to the groin area. The male member then is inserted through the channel (in the direction of arrow 502), and the pad is folded around the male member to make a pocket, primarily composed of outer permeable layer 550.

For example, male incontinence pad 500 can folded on one side towards the distal end of the male member and then the opposite side towards the distal end of the male member. This causes outer permeable layer 550 to form a pocket (e.g., partial for full) for the distal end of the male member. The edges of the folded portions of the outer permeable layer 550 can be in proximity to each other or overlap each other. Pad 500 can then be folded along another side towards the distal end of be male member and then the opposite side towards the distal end of the male member, which will complete or reinforce the pocket for the male member. Portions of the pad from the third fold and from the fourth fold can be in proximity to each other or overlap each other. If desired, an incontinence brief can then be placed over the pad, which will better maintain the shape and/or position of pad 500.

In particular implementations, outer permeable layer 510 can include a fastening system, such as described above. The fastening system can, for example, include a first attachment zone and a second attachment zone. The attachment zones can, for instance, be parts of a hook-and-loop fastening system. In particular implementations, the attachment zones can be composed of a number of individual sections. In other implementations, the fastening system can include pins, snaps, and/or buttons.

During operation, the distal end of the male member should remain in the pocket formed by outer. Thus, if there is any discharge, inner absorbent layer 540 operates to absorb this. Moreover, inner lining 530 operates to reduce the likelihood or prevent the discharge from reaching the wearer. If, however, the male member should come out from the pocket (e.g., due to movement or shrinkage), inner absorbent layer 520 operates to assist in absorbing any discharge. The absorbency will typically not be as good as if the male member remained in the pocket, but the pad will operate to absorb all or a substantial portion of the discharge. In particular implementations, the pad inner absorbent layer 520 and the inner absorbent layer 540 can absorb about 1.5 liters in combination.

Pad 500 has a variety of features. For example, the pad operates to completely or substantially absorb discharge from the wearer. Thus, when it is time to tend to the wearer, the task is much easier, as the pad can be removed simply and only minimal cleanup around the male member will be required. Moreover, a new pad can be readily fitted. In contrast, when a wearer only uses a full-size incontinence brief, the entire brief must be which requires a substantial amount of physical effort. Moreover, for individuals that require regular hydration (e.g., through an IV), this may mean that they need to be tended to every few hours. Having to change a full-size brief every few hours is a very labor-intensive task. The male incontinence pad of the subject invention operates to prevent or reduce the likelihood of bed sores in the groin area due to the fact that the pad is easy to replace and the patient will not have to lie wet with urine for long periods of time in the region surrounding the entire groin area. This is especially true if the pad is being changed frequently, as it should be, which may be more likely since the changing process is greatly simplified.

Moreover, the pad may cost quite a bit less than a typical incontinence brief, which may save the caregiver money. Another benefit is that wearers would not have to rely as much on catheters, which can cause quite a bit of pain and discomfort and can lead to urinary tract infections.

Although FIG. 5 illustrates an example male incontinence pad, other embodiments of the male incontinence pads can have fewer, additional, or a different arrangement of components. For example, outer permeable layer 510 can include a fastening system (e.g., one or more attachment zones) such as described above. Moreover, an attachment zone can be placed on the outer permeable layer 550. Additionally, a different type of fastening system (e.g., pins) can be used. As another example, additional pads/layers can be used. In one example, inner absorbent layer 540 can have extra absorbency in the middle of the pad. Additionally, although four folds have been discussed for using the illustrated implementation, other modes of operation or implementations can allow for fewer or more folds.

In particular implementations, the inner liner 530 can have small openings (e.g., slits) 150 therein, such as shown in FIGS. 1 and 3. These openings can operate to allow liquid to flow from the inner absorbent layer 540 to the inner absorbent layer 520. By allowing liquid to flow from the inner absorbent layer 540 to the inner absorbent layer 520, the openings operate to assist in preventing leakage once the inner pad reaches its limit of absorption, by transferring the extra liquid into the outer pad. Additionally, the outer permeable layer 510 can include a wetness indicator, and the openings in the inner liner operates to allow the wetness indicator to function. Upon detecting wetness, the indicator operates to provide a signal, such as a visual signal (e.g., color change). The wetness indicator can, for example, operate using a pH zone (e.g., litmus).

Figure 6:
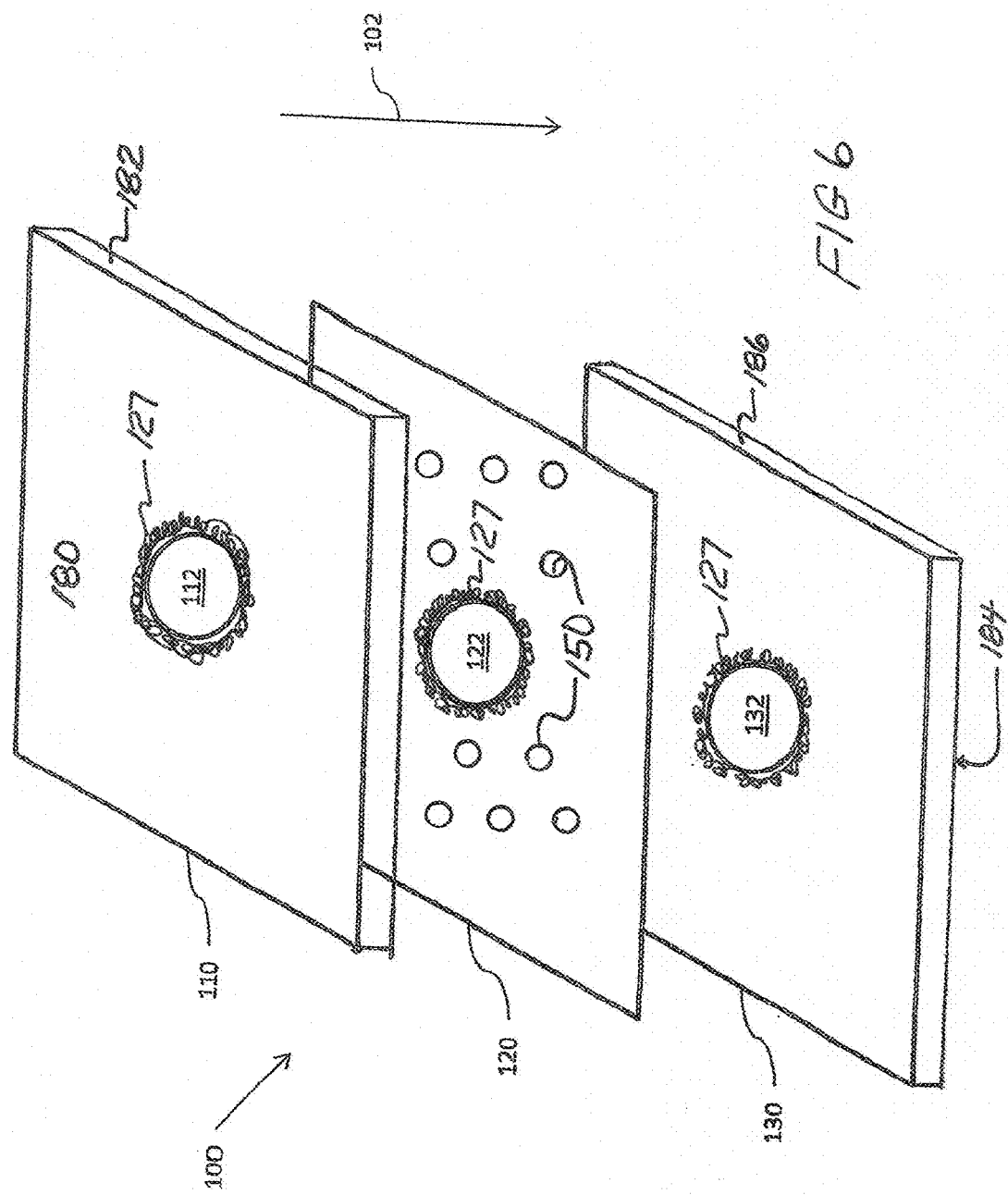
FIG. 6 is a line drawing showing an elastic component positioned around the periphery of the channel formed from apertures in the outer pad, lining and inner pad for receiving a male member and operates to expand or contract to maintain contact of the pad around the male member.

In other preferred embodiments of the invention, as illustrated in FIG. 6, the channel 125 includes an elastic component 127 positioned around the periphery of the channel 125 for receiving a male member and operates to provide elasticization of the channel allowing it to expand or contract to maintain contact of the pad around the male member. The elastic component 127 further operates to maintain a proper fit and reduces the likelihood that the male member will come out of the pocket formed when the pad is folded around the male member such as due to movement or shrinkage of the male member. It should be understood that the contractive forces being exerted radially towards the male member of the elastic component should be great enough to maintain a proper fit while allowing the pad to fit comfortably on the patient. It should be apparent to one skilled in the art that the elastic component can be formed from a variety of materials having suitable elastic properties and can include, but not limited to, Lycra®, spandex material, and elastic yarns. It should also be apparent that the elastic component 127 can be positioned around the periphery of one or more of the apertures 112, 122, 132, as shown.

Figure 7:
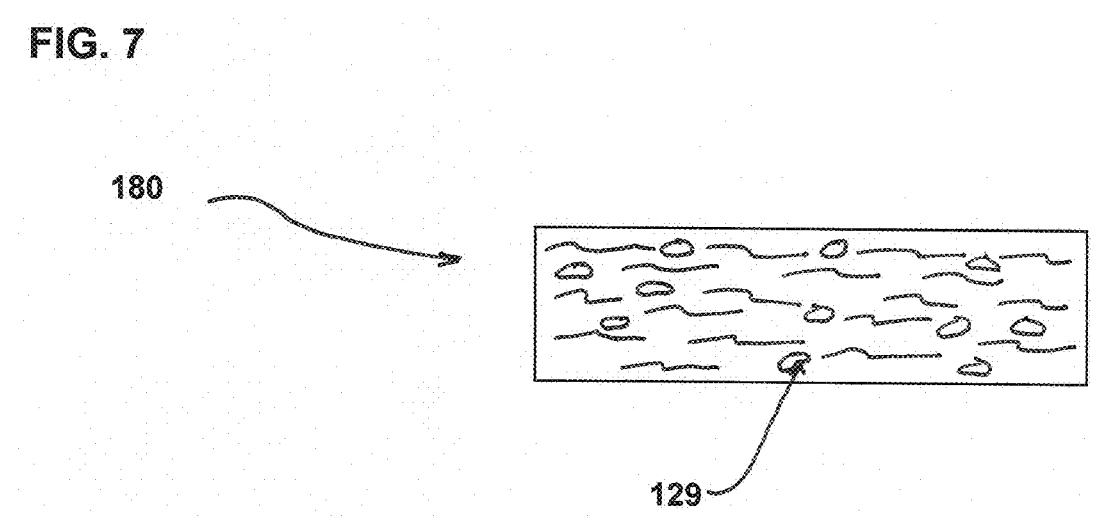
FIG. 7 is a schematic illustration showing a skin care agent contained within or along the surface of the outer permeable layer of the outer pad.
Figure 8:
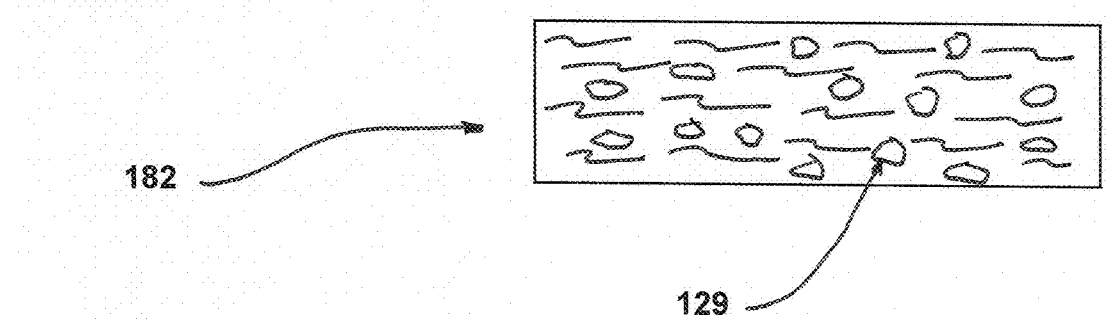
FIG. 8 is a schematic illustration showing a skin care agent contained within the inner absorbent layer of the outer pad.
Figure 9:
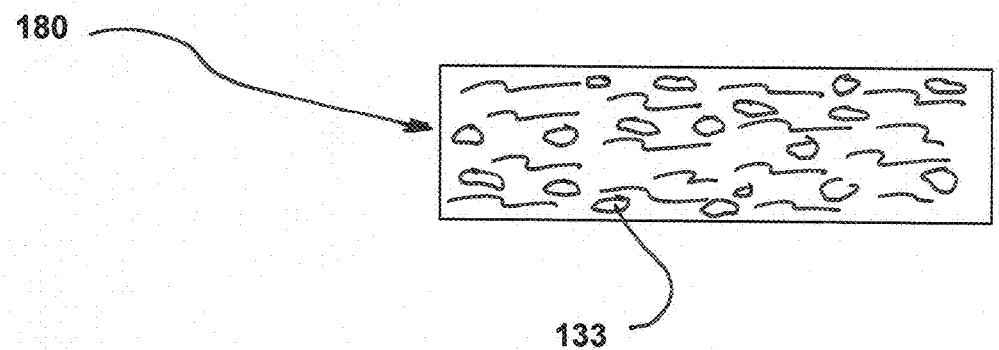
FIG. 9 is a schematic illustration showing the skin care agent having copper or a copper alloy.

The preferred embodiments of the subject invention, as illustrated in FIGS. 7 and 8, the male incontinence pad of the subject invention includes a skin care agent 129 contained within the outer permeable layer 180 or the inner absorbent layer 182 of the outer pad 110. In one preferred embodiment the skin care agent 129, such as a lotion, skin care composition and/or therapeutic composition typically utilized for use in baby diapers, and is applied to at least a portion of the outer surface 131 of the outer permeable layer 180. In another preferred embodiment the skin care agent 129 is contained within inter-fiber spaces of the inner absorbent layer 182 and has a consistency that permits it to pass through the outer permeable layer and contact the skin of the wearer to form a protective wetness barrier. Preferably, the skin care agent operates to suppress the occurrence of rash and inflammation and if rash or inflammation occurs, suppresses the progress of the rash or inflammation or relaxes the rash or inflammation. In a preferred embodiment, as illustrated in FIG. 9, the skin care agent can also reduce the likelihood of bacterial growth and includes a copper or copper alloy component 133 and can be in the form of copper or copper alloy threads, fibers or powers (particles, as shown) that are interwoven or incorporated along the outer permeable layer 180 that operate to reduce the growth of bacteria.

Figure 10:
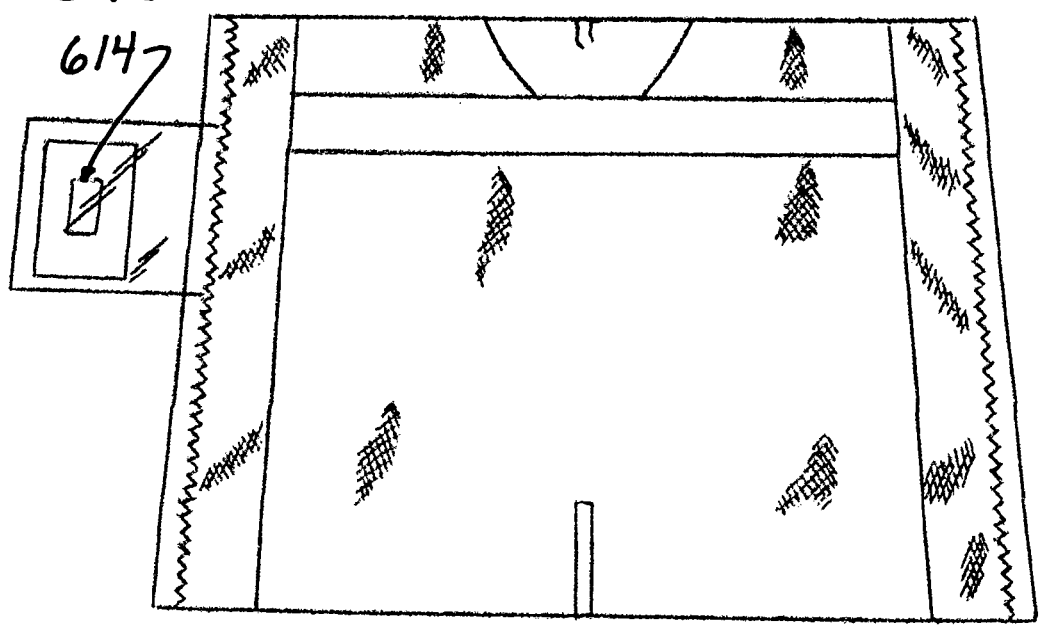
FIG. 10 is an image of another preferred embodiment of the male incontinence pad in its folded configuration showing the outer absorbent pad and a fastening system.
Figure 11:
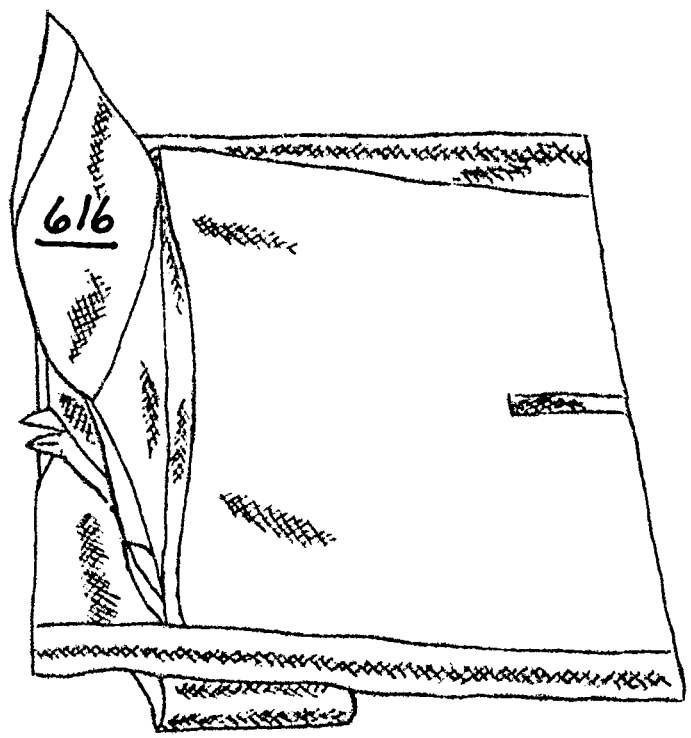
FIG. 11 is an image showing the male incontinence pad of FIG. 10 showing the flap for use in covering the male member when the male member has been inserted into the pad.
Figure 12:
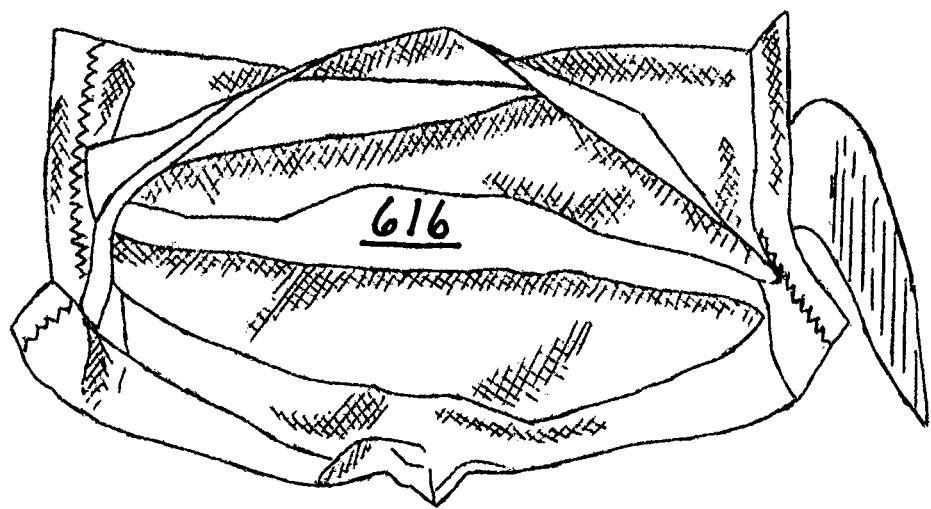
FIG. 12 is an image showing the male incontinence pad of FIG. 10 showing the inner pocket for receiving a male member.
Figure 13:
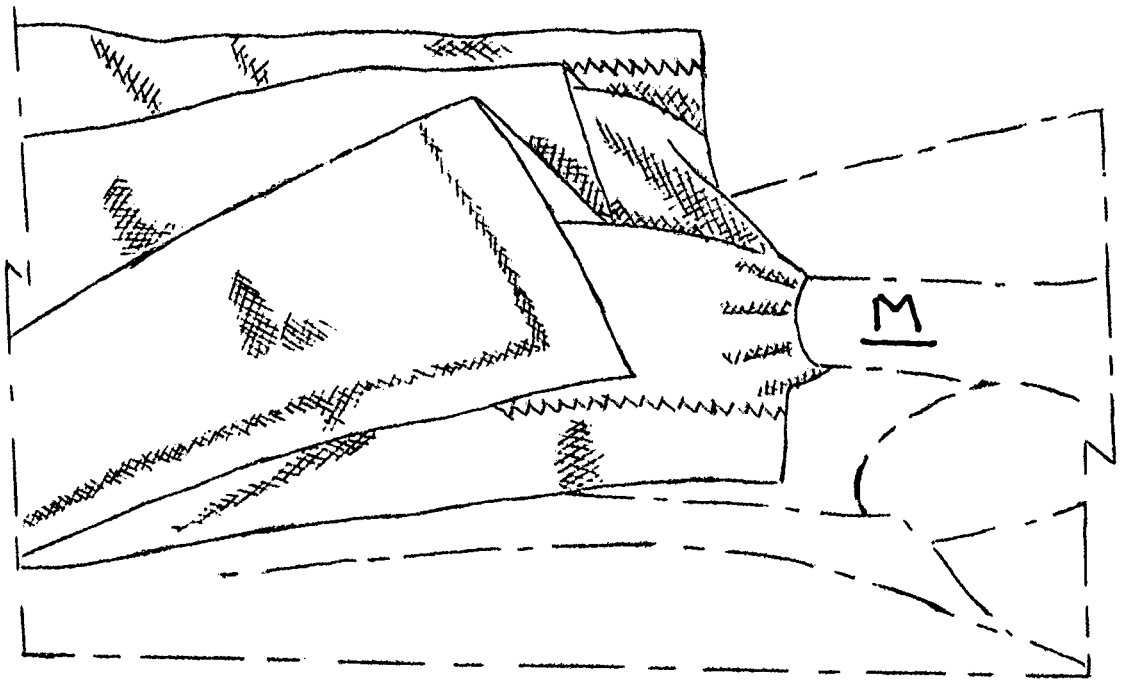
FIG. 13 is an image showing the male incontinence pad of FIG. 10 showing a male member being inserted through a channel and extending into the inner pocket.
Figure 14:
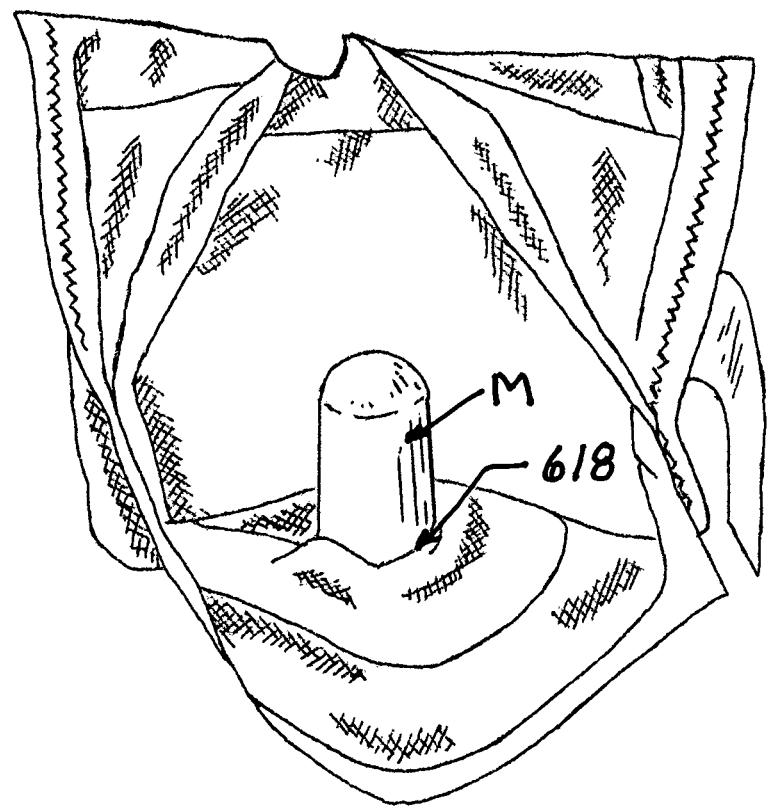
FIG. 14 is an image showing the male incontinence pad of FIG. 10 showing the male member positioned within the inner pocket.
Figure 15:
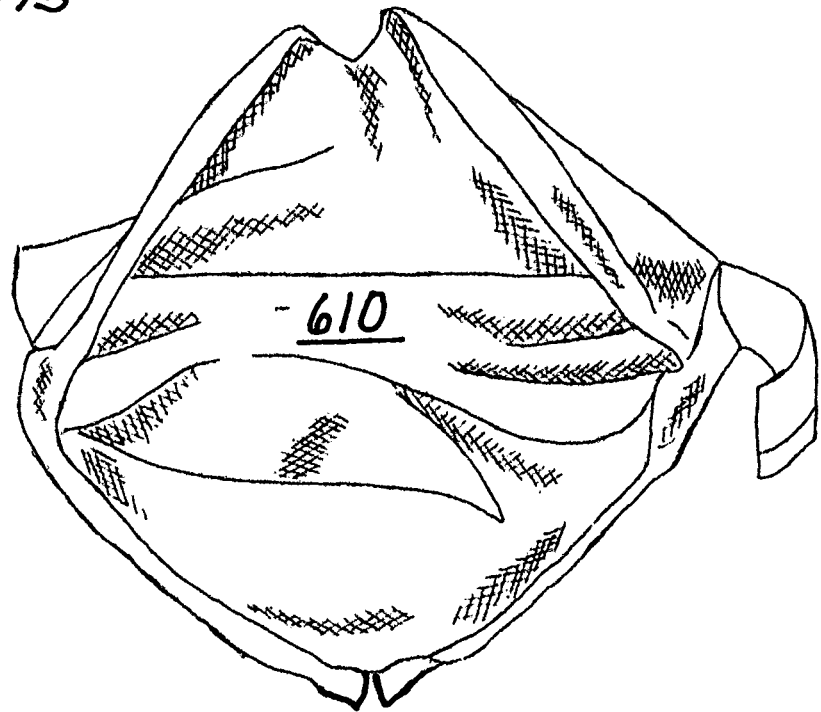
FIG. 15 is an image showing the male incontinence pad of FIG. 10 showing the male member positioned within the inner pocket with the flap folded over the male member.
Figure 16:
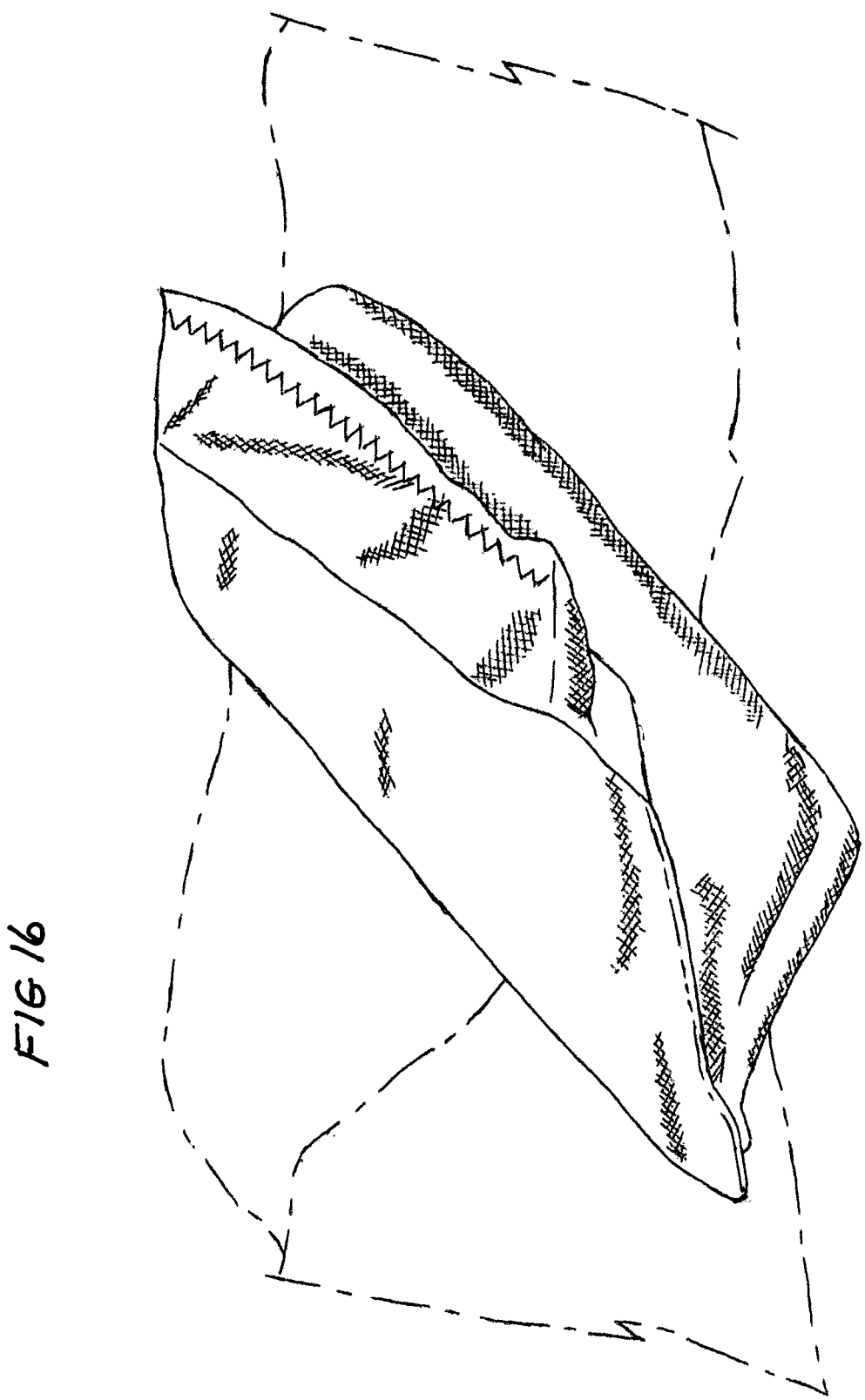
FIG. 16 is an image showing the male incontinence pad of FIG. 10 showing the male incontinence pad in its folded position around the male member and held in its folded position by the fastening system.

In another preferred embodiment of the invention the male incontinence pad 600 can be formed a folded configuration to receive a male member. As illustrated in FIGS. 10-17, the pad 600 includes an outer absorbent pad 602 and an inner absorbent pad 604 that are folded such that apertures 623, 625, 627, 637 and 635 (FIG. 16) are positioned at the edge of the incontinence pad, such as shown in FIG. 10 leaving extensions 616a-616e that connected together form an outwardly extending flap 616 (FIG. 11). The peripheral edges of the outer absorbent pad 602 and the inner absorbent pad 604 are attached together leaving an open end 608 forming an inner pocket 610, such as shown in FIG. 12, so that the outer absorbent pad 602 is positioned on the outside of the male incontinence pad 600. Attached to the outer surface 612 of the outer absorbent pad 602 is a fastening system 614. As illustrated in FIG. 11, the folding of the inner absorbent pad 604 and the outer absorbent pad 602 produces and an outwardly flap 616. In operation, as illustrated in FIGS. 13 and 14, a male member M is inserted through the channel 618 created by aligned apertures 623, 625, 627, 637 and 635 such that it extends into the inner pocket 610. Once inserted, flap 618 folds inwardly into the inner pocket 610 such that it lays against and covers the male member M (FIG. 15). The pad 600 can then be folded around the male member, such as illustrated in FIG. 16 and held in its folded position the fastening system 614 which attaches to the outer absorbent pad 602.

Figure 17:
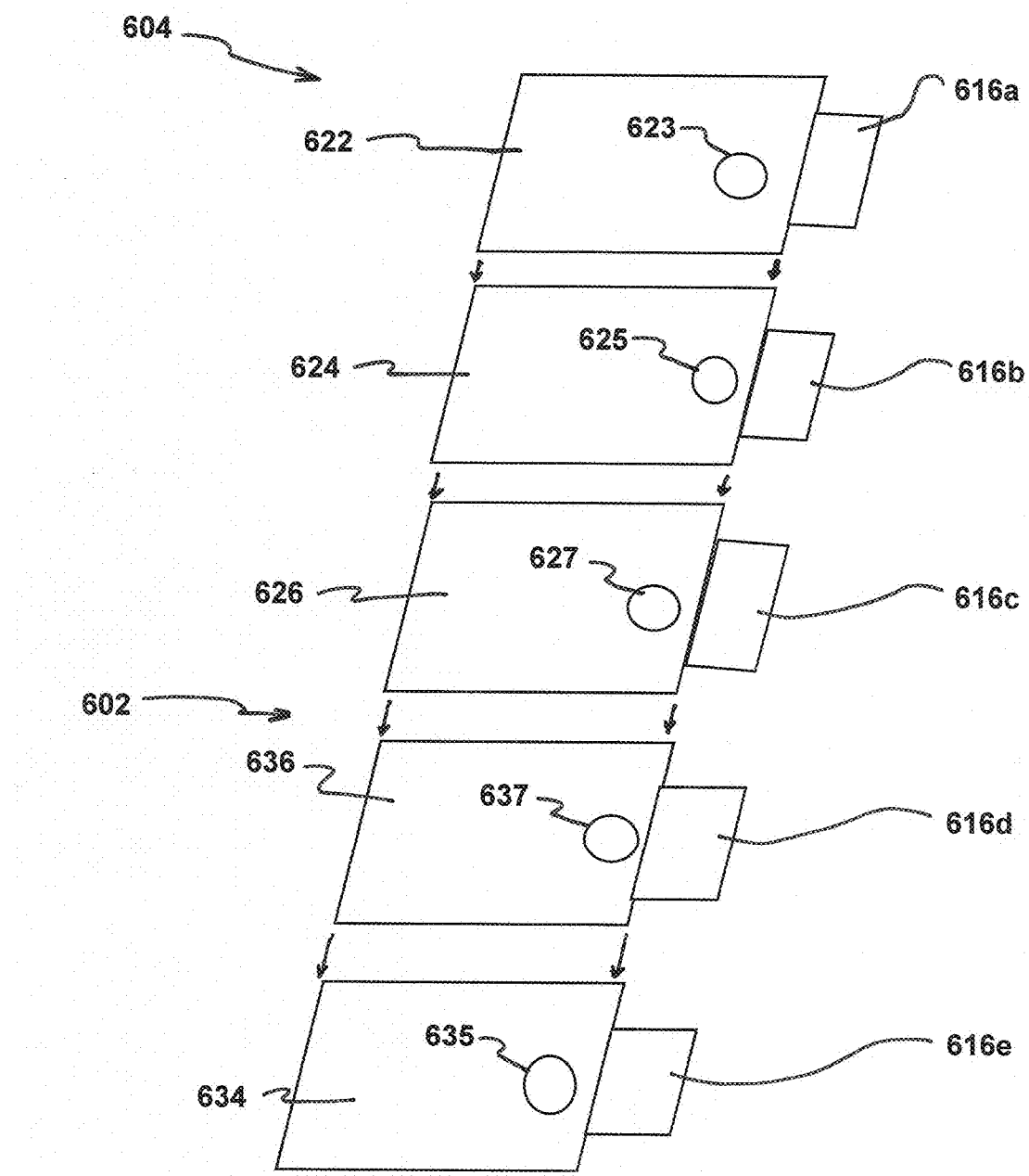
FIG. 17 is a schematic illustration showing the various layers forming the inner absorbent pad and the outer absorbent pad.

In a preferred embodiment, as illustrated in FIG. 17, the inner absorbent pad 604 includes liquid permeable layer 622, such as a polypropylene hydrophilic material (one such material is PGI 0326-004h White SMS polypropylene hydrophilic material sold by Polymer Group Company of Charlotte, N.C.) having an aperture 623, a wicking layer 624 made from cotton fibers or synthetic polymers or a hydrophilic polymer and a fibrous material such as wood pulp (One such material is a 356 Airtex material, sold by Georgia Pacific of Atlanta, Ga.) having a aperture 625 and a SAP core layer 626 having an aperture 627 and formed from super absorbent polymers or slush powders, hydrogels, or other super-absorbent material(s) (collectively referred to as SAP material). One such material is Gelok 18040 material sold by Gelok International Corporation of Dunbridge, Ohio. The outer absorbent pad 602 and the inner absorbent pad 604 are attached together along their outer peripheries leaving an open end. The liquid permeable layer 622 is further attached to the wicking layer 624 along the peripheries of the apertures 623 and 625. It should be understood that by only attaching the liquid permeable layer 622 and the wicking layer 624 only along the periphery of the apertures 623 and 625 and the periphery of the layers allows liquid to flow more quickly and evenly along the surface of the wicking layer thereby improving the ability of the wicking layer to spread and absorb liquid. The wicking layer 624 is further attached to the SAP core layer 626, such as by glue, or a glue sheet (such as Savare TH70 sold by Savare Specialty Adhesives of Delaware, Ohio) or other suitable means that allows liquid to flow from the wicking layer to the SAP core layer. In operation, the wicking layer 624 operates to spread liquid discharge from the male member along the SAP core layer 626 such as by wicking or capillary action. In a preferred embodiment an elastic component can be applied to the liquid permeable layer or around the periphery of channel 616 to maintain a proper fit around the male member such as due to movement or shrinkage of the male member thereby reducing the likelihood of fluid leakage from around the male member during use.

In a preferred embodiment, the outer absorbent pad 602 includes an outer hook attachment layer 634 further attached to a liquid impermeable layer 636, such as by glue or by a glue sheet (such as a Savare TF70 glue sold by Savare Specialty Adhesives of Delaware, Ohio) or other suitable means. The hook attachment layer cooperates with the fastening system to maintain the male incontinence pad in its folded position around the male member. In a preferred embodiment, the fastening system and the hook attachment layer use a hook and loop system that allows the fastening system to easy attach to the outer absorbent pad allowing the male incontinence pad to be in a tight or a more-folded configuration. The liquid impermeable layer 636 is further attached to the SAP core layer 626 using a glue or a glue sheet (such as Savare TH70 sold by Savare Specialty Adhesives of Delaware, Ohio) or other suitable means. The hook attachment layer 634 is preferably a soft polypropylene spunbond material such as sold by Berry Global, Inc. of Evansville, Ind., product no. J1550448. During use, the liquid impermeable layer 636 operates to prevent liquid from penetrating outside the male incontinence pad. Preferably the liquid impermeable sheet is made of a nonwoven fabric, such as plastic resins made from nylon, polyester, polyethylene, or polypropylene. One such material is sold under Filmtech White FT935E by Filmtech Inc. of Bean Station, Tenn.

The pads discussed herein has mainly been discussed with respect to adults, but they may also be useful for males of other ages (e.g., boys). In general, the pads may be useful for any male who happens to be in a setting (e.g., hospital, nursing home, or home care) and are in briefs (diapers) and unable to care for their private need of urinating on their own.

Although the invention has been described with reference to specific implementations, this description is not meant to be construed in a limiting sense. On the contrary, various modifications of the disclosed implementations will be readily apparent to those skilled in the art upon reference to the written description and drawings. The scope of the protected subject matter should therefore be judged based on the following claims, which may encompass one or more aspects of one or more implementations.

The invention claimed is:

1. A male incontinence pad for use by a male wearer, the male incontinence pad comprising:
    an inner absorbent pad having an aperture;
    an outer absorbent pad having formed from an outer liquid permeable layer and an inner absorbent layer and having an aperture through said outer absorbent pad; and
    a liquid impermeable inner lining between said inner absorbent pad and said outer absorbent pad, said inner lining having an aperture;
    wherein said inner absorbent pad and said outer absorbent pad are attached together to form an inner pocket;
    wherein said aperture of said inner absorbent pad and said aperture of said outer absorbent pad and said aperture of said inner liner are aligned to form a channel such that a male member may be placed therethrough; and
    wherein said channel having an elastic component that operates to provide elasticization to maintain contact of the male incontinence pad with said male member when male member is positioned within said channel and said inner pocket.

2. The male incontinence pad of claim 1 further comprising an outwardly extending flap that operates to fold inwardly into said inner pocket such that said flap lays against the male member positioned within said inner pocket.

3. The male incontinence pad of claim 1 wherein male incontinence pad further comprises a fastening system to maintain the male member within said inner pocket.

4. The male incontinence pad of claim 1 wherein said inner absorbent pad includes an SAP core layer.

5. The male incontinence pad of claim 1 wherein said inner lining includes openings that operate to allow liquid to pass from said inner absorbent pad to said outer absorbent pad.

6. The male incontinence pad of claim 1 further comprising a wetness indicator that operates to signal wetness.

7. The male incontinence pad of claim 1 further comprising a skin care agent that operates to form a wetness barrier between the male incontinence pad and the male member.

8. The male incontinence pad of claim 1 further comprising a skin care agent that operates to reduce bacteria growth.

9. The male incontinence pad of claim 1 further comprising a skin care agent comprising copper or a copper alloy that operates to reduce bacteria growth.

10. A male incontinence pad for use by a male wearer, the male incontinence pad comprising:
    an inner absorbent pad having an aperture;
    an outer absorbent pad having an aperture;
    a liquid impermeable inner lining between said inner absorbent pad and said outer absorbent pad, said inner lining having an aperture; and
    a skin care agent that operates to form a wetness barrier between the male continence pad and the mate member and operates to reduce bacteria growth;
    wherein said inner lining includes openings that operate to allow liquid to pass from said inner absorbent pad to said outer absorbent pad; and
    wherein said aperture of said inner absorbent pad and said aperture of said outer absorbent pad and said aperture of said inner liner are aligned to form a channel such that a male member may be placed therethrough.

11. The male incontinence pad of claim 10 wherein said skin care agent comprises copper or a copper alloy.

12. A male incontinence pad for use by a male wearer, the male incontinence pad comprising:
    an inner absorbent pad having an aperture, wherein said inner absorbent pad is formed from a liquid permeable outer layer and an absorbing inner layer;
    an outer absorbent pad having an aperture and formed from a liquid permeable outer layer and an absorbing inner layer;
    a liquid impermeable inner lining between said inner absorbent pad and said outer absorbent pad, said inner lining having an aperture;
    a skin care agent that operates to form a wetness barrier between the male incontinence pad and the male member; and wherein said liquid impermeable inner liner includes openings that operate to allow liquid to pass from said inner absorbent pad to said outer absorbent pad;

wherein said aperture of said inner absorbent pad and said aperture of said outer absorbent pad and said aperture of said inner liner are aligned to form a channel such that a male member may be placed therethrough;

wherein said outer absorbent pad is adapted to fold around the male member to form a pocket when the male member is positioned within said channel and wherein said male incontinence pad further comprises a fastening system to maintain said pocket; and wherein said channel having an elastic component that operates to provide elasticization to maintain contact of the male incontinence pad with said male member when said male member is positioned within said channel.

13. The male incontinence pad of claim 12 wherein said skin care agent operates to reduce bacteria growth.

14. The male incontinence pad of claim 13 wherein said skin care agent comprises copper or a copper alloy.

15. A male incontinence pad for use by a male wearer, the male incontinence pad comprising:
an inner absorbent pad;
an outer absorbent pad;
an inner lining between said inner absorbent pad and said outer absorbent pad;
wherein said outer absorbent pad and said inner absorbent pad are attached together having an open end forming an inner pocket and an outwardly extending flap;
wherein said inner absorbent pad, said inner lining and said outer absorbent pad each having an aperture that together form a channel that extends into said inner pocket;
wherein said inner lining is adapted to allow liquid to pass from said inner absorbent pad to said outer absorbent pad;
wherein when a male member is inserted through said channel the male member extends into said inner pocket; and
wherein when the male member extends into the inner pocket, said outwardly extending flap operates to fold over the male member.

16. The male incontinence pad of claim 15 wherein said inner absorbent pad and said outer absorbent pad operate to fold around the male member and includes a fastening system for maintaining said inner absorbent pad and said outer absorbent pad in position folded around the male member.

17. The male incontinence pad of claim 16 wherein said inner absorbent pad includes a liquid permeable layer and a wicking layer and a SAP core layer.

18. The male incontinence pad of claim 16 wherein said outer absorbent pad includes an outer attachment layer attached to a liquid impermeable layer and wherein said liquid impermeable layer is attached to a SAP core layer.

* * * * *